US008017725B2

(12) United States Patent
Chiquet-Ehrismann et al.

(10) Patent No.: US 8,017,725 B2
(45) Date of Patent: Sep. 13, 2011

(54) USE OF HEPARIN-BINDING DOMAIN OF FIBRONECTIN FOR DIAGNOSIS AND TREATMENT OF CANCER

(75) Inventors: Ruth Chiquet-Ehrismann, Reinach (CH); Gertraud Orend, Pratteln (CH)

(73) Assignee: Novartis Forschungesstiftung Zweigniederlassung Friedrich Miescher Institute for Biomedical Research, Basel (CH)

( * ) Notice: Subject to any disclaimer, the term of this patent is extended or adjusted under 35 U.S.C. 154(b) by 264 days.

(21) Appl. No.: 11/522,630

(22) Filed: Sep. 18, 2006

(65) Prior Publication Data

US 2007/0225222 A1    Sep. 27, 2007

Related U.S. Application Data

(63) Continuation of application No. 10/485,924, filed as application No. PCT/EP02/08881 on Aug. 8, 2002, now abandoned.

(30) Foreign Application Priority Data

Aug. 9, 2001    (GB) .................................. 0119476.0

(51) Int. Cl.
*A61K 38/00* (2006.01)
(52) U.S. Cl. .......................................... 530/300; 514/12
(58) Field of Classification Search .................. None
See application file for complete search history.

(56) References Cited

U.S. PATENT DOCUMENTS

| | | | | |
|---|---|---|---|---|
| 5,641,483 | A | 6/1997 | Beaulieu | 424/78.06 |
| 5,679,230 | A | 10/1997 | Fatcheric et al. | 205/50 |
| 5,750,378 | A | 5/1998 | Goodheart et al. | 435/70.3 |
| 5,958,874 | A | 9/1999 | Clark et al. | 514/2 |
| 6,025,150 | A | 2/2000 | Livant | 435/29 |
| 6,060,317 | A | 5/2000 | Malech | 435/456 |
| 6,180,610 | B1 | 1/2001 | Ruoslahti et al. | 514/17 |
| 6,194,378 | B1 | 2/2001 | Clark et al. | 514/2 |

FOREIGN PATENT DOCUMENTS

| | | |
|---|---|---|
| EP | 0 399 806 | 11/1990 |
| EP | 0428266 | 5/1991 |
| EP | 0 837 074 A2 | 4/1998 |
| EP | 0837074 | 4/1998 |
| EP | 1033405 A2 * | 9/2000 |
| JP | 05271291 | 10/1993 |
| JP | 10-29952 | 3/1998 |
| WO | WO 8901942 | 3/1989 |
| WO | WO 94/13692 | 6/1994 |
| WO | WO 00/55181 | 9/2000 |
| WO | WO 01/72776 A2 | 10/2001 |

OTHER PUBLICATIONS

Bloom et al., Fibronectin regulates assembly of actin filaments and focal contacts in cultured cells via heparin binding site in repeat III13, Molecular Biology of the Cell, vol. 10, pp. 1521-1536, 1999.*
Chung et al., Binding tenascin C to soluble fibronectin and matrix fibrils, J. Biological Chemistry, vol. 270, No. 48, pp. 29012-29017, 1995.*
Akamatsu et al., "Suppression of Transformed Phenotypes of Human Fibrosarcoma Cells by Overexpression of Recombinant Fibronectin", Cancer Res, vol. 56, No. 19, pp. 4541-4546 (1996).
Akiyama, Olden and Yamada, "Fibronectin and Integrins in Invasion and Metastasis", Cancer Metastasis Rev, vol. 14, No. 3, pp. 173-189 (1995).
Asakura et al., "Opposing Effects of Low and High Molecular Weight Kininogens on Cell Adhesion", J Biochem (Tokyo), vol. 124, No. 3, pp. 473-484 (1998).
Basic and Clinical Immunology, 7th Edition, Stites and Terr, Eds., Appleton and Lange, 870 pages, Norwalk, CT (1991).
Barnea et al., "Receptor Tyrosine Phosphatase β is Expressed in the Form of Proteoglycan and Binds to the Extracellular Matrix Protein Tenascin", J Biol Chem, vol. 269, No. 20, pp. 14349-14352 (1994).
Bauer et al., "Motility of Fibronectin Receptor-Deficient Cells on Fibronectin and Vitronectin: Collaborative Interactions Among Integrins", J Cell Biol, vol. 116, No. 2, pp. 477-487 (1992).
Bloom, Ingham and Hynes, "Fibronectin Regulates Assembly of Actin Filaments and Focal Contacts in Cultured Cells Via the Heparin-Binding Site in Repeat III$_{13}$", Mol Biol Cell, vol. 10, No. 5, pp. 1521-1536 (1999).
Borsi et al., "Expression of Different Tenascin Isoforms in Normal, Hyperplastic and Neoplastic Human Breast Tissues", Int J Cancer, vol. 52, No. 5, pp. 688-692 (1992).
Boudreau and Bissell, "Extracellular Matrix Signaling: Integration of Form and Function in Normal and Malignant Cells", Curr Opin Cell Biol, vol. 10, No. 5, pp. 640-646 (1998).
Chan and-White, Eds, "Fmoc Solid Phase Peptide Synthesis: A Practical Approach", Oxford University Press, 680 pages (2000).
Chiquet and Fambrough, "Chick Myotendinous Antigen. II. A Novel Extracellular Glycoprotein Complex Consisting of Large Disulfide-Linked Subunits", J Cell Biol, vol. 98, No. 6, pp. 1937-1946 (1984).
Chiquet-Ehrismann, Mackie, Pearson and Sakakura, "Tenascin: An Extracellular Matrix Protein Involved in Tissue Interactions During Fetal Development and Oncogenesis", Cell, vol. 47, No. 1, pp. 131-139 (1986).
Chiquet-Ehrismann et al., "Tenascin Interferes with Fibronectin Action", Cell, vol. 53, No. 3, pp. 383-390 (1988).
Chiquet-Ehrismann and Chiquet, "Tenascins: Regulation and Putative Functions During Pathological Stress", J Pathol, vol. 200, No. 4, pp. 488-499 (2003).

(Continued)

Primary Examiner — Suzanne M. Noakes
(74) Attorney, Agent, or Firm — Hoxie & Associates LLC

(57) ABSTRACT

The FNIII13 domain of fibronectin and smaller fragments thereof have a tumour cell proliferation inhibitory effect. Compositions are provided comprising fragments of fibronectin having the FNIII 13 domain and fragments thereof. A system comprising cells exposed to fibronectin and caused to proliferate by the presence of tenascin are used as an in vitro method for screening possible anti-tumour agents. Cell-free systems comprising a fibronectin ligand and tenascin are also employed for screening potential anti-tumour or anti-cancer agents. Test compounds are assayed for the ability to disrupt binding of the fibronectin ligand to tenascin. A further cell-free system additionally includes a syndecan molecule.

9 Claims, No Drawings

OTHER PUBLICATIONS

Chung and Erickson, "Glycosaminoglycans Modulate Fibronectin Matrix Assembly and Are Essential for Matrix Incorporation of Tenascin-C", *J Cell Sci*, vol. 110, Pt. 12, pp. 1413-1419 (1997).
Cote et al., "Generation of Human Monoclonal Antibodies Reactive with Cellular Antigens", *Proc Natl Acad Sci USA*, vol. 80, No. 7, pp. 2026-2030 (1983).
*Current Protocols in Immunology*, Coligan et al., Eds., John Wiley & Sons, Inc., NY (1991).
Fischer, Chiquet-Ehrismann, Bemasconi and Chiquet, "A Single Heparin Binding Region Within the Fibrinogen-Like Domain is Functional in Chick Tenascin-C", *J Biol Chem*, vol. 270, No. 7, pp. 3378-3384 (1995).
Fischer, Lüdi, Schulthess and Chiquet-Ehrismann, "Concerted Action of Tenascin-C Domains in Cell Adhesion, Anti-Adhesion and Promotion of Neurite Outgrowth", *J Cell Sci*, vol. 110, Pt. 13, pp. 1513-1522 (1997).
Fischer, Tucker, Chiquet-Ehrismann and Adams, " Cell-Adhesive Responses to Tenascin-C Splice Variants Involve Formation of Fascin Microspikes", *Mol Biol Cell*, vol. 8, No. 10, pp. 2055-2075 (1997).
Giancotti and Ruoslahti, " Elevated Levels of the $\alpha_5\beta_1$ Fibronectin Receptor Suppress the Transformed Phenotype of Chinese Hamster Ovary Cells", *Cell*, vol. 60, No. 5, pp. 849-859 (1990).
Gong et al., "Role of $\alpha_5\beta_1$ Integrin in Determining Malignant Properties of Colon Carcinoma Cells", *Cell Growth Differ*, vol. 8, No. 1, pp. 83-90 (1997).
Gong, Ko and Brattain, "Disruption of Fibronectin Binding to the $\alpha_5\beta_1$ Integrin Stimulates the Expression of Cyclin-Dependent Kinases and DNA Synthesis Through Activation of Extracellular Signal-Regulated Kinase", *J Biol Chem*, vol. 273, No. 3, pp. 1662-1669 (1998).
Grumet et al., "Interactions with Tenascin and Differential Effects on Cell Adhesion of Neurocan and Phosphacan, Two Major Chondroitin Sulfate Proteoglycans of Nervous Tissue", *J Bid Chem*, vol. 269, No. 16, pp. 12142-12146 (1994).
Huang et al., " Interference of Tenascin-C with Syndecan-4 Binding to Fibronectin Blocks Cell Adhesion and Stimulates Tumor Cell Proliferation", *Cancer Res*, vol. 61, No. 23, pp. 8586-8594 (2001).
Huse et al., "Generation of A Large Combinatorial Library of the Immunoglobulin Repertoire in Phage Lambda", *Science*, vol. 246, No. 4935, pp. 1275-1281 (1989).
Hynes, "Cell Adhesion: Old and New Questions", Trends Cell Biol, vol. 9, No. 12, pp. M33-M37 (1999).
Jahkola et al., "Expression of Tenascin-C in Intraductal Carcinoma of Human Breast: Relationship to Invasion", *Eur J Cancer*, vol. 34, No. 11, pp. 1687-1692 (1998).
Kawakatsu et al., "Human Carcinoma Cells Synthesize and Secrete Tenascin In Vitro", *Jpn J Cancer Res*, vol. 83, No. 10, pp. 1073-1080 (1992).
Klass, Couchman and Woods, "Control of Extracellular Matrix Assembly by Syndecan-2 Proteoglycan", *J Cell Sci*, vol. 113, Pt. 3, pp. 493-506 (2000).
Koehler and Milstein, "Continuous Cultures of Fused Cells Secreting Antibody of Predefined Specificity", *Nature*, vol. 256, pp. 495-497 (1975).
Kohfeldt, Maurer, Vannahme and Timpl, "Properties of the Extracellular Calcium Binding Module of the Proteoglycan Testican", *FEBS Lett*, vol. 414, No. 3, pp. 557-561 (1997).
Komblihtt, Umezawa, Vibe-Pedersen and Baralle, "Primary Structure of Human Fibronectin: Differential Splicing May Generate at Least 10 Polypeptides From a Single Gene", *EMBO J*, vol. 4, No. 7, pp. 1755-1759 (1985).
Kozbor and Roder, "The Production of Monoclonal Antibodies From Human Lymphocytes", *Immunol Today*, vol. 4, No. 3, pp. 72-79 (1983).
Liu et al., "Heparan Sulfate Proteoglycans as Adhesive and Anti-Invasive Molecules", *J Biol Chem*, vol. 273, No. 35, pp. 22825-22832 (1998).
Lotz, Burdsal, Erickson and McClay, "Cell Adhesion to Fibronectin and Tenascin: Quantitative Measurements of Initial Binding and Subsequent Strengthening Response", *J Cell Biol*, vol. 109, No. 4, Pt. 1, pp. 1795-1805 (1989).

McFall and Rapraeger, "Characterization of the High Affinity Cell-Binding Domain in the Cell Surface Proteoglycan Syndecan-4", *J Biol Chem*, vol. 273, No. 43, pp. 28270-28276 (1998).
*Methods in Cell Biology*, vol. 37: Antibodies in Cell Biology, Asai, Ed., Academic Press, Inc., NY (1993).
Milev et al., "Interactions of the Chondroitin Sulfate Proteoglycan Phosphacan, the Extracellular Domain of a Receptor-Type Protein Tyrosine Phosphatase, with Neurons, Glia, and Neural Cell Adhesion Molecules", *J Cell Biol*, vol. 127, No. 6, Pt. 1, pp. 1703-1715 (1994).
*Monoclonal Antibodies and Cancer Therapy*, Cole et al., Eds., Alan R Liss, Inc., New York, NY, pp. 77-96 (1985).
*Monoclonal Antibodies: Principles and Practice*, 2nd Edition, Goding, Ed., Academic Press, New York, NY (1986).
Norderhaug, Olafsen, Michaelsen and Sandlie, "Versatile vectors for transient and stable expression of recombinant antibody molecules in mammalian cells", *J Immunol Methods*, vol. 204, No. 1, pp. 77-87 (1997).
Oh, Woods and Couchman, "Multimerization of the Cytoplasmic Domain of Syndecan-4 is Required for Its Ability to Activate Protein Kinase C", *J Biol Chem*, vol. 272, No. 18, pp. 11805-11811 (1997).
Orend et al., "Tenascin-C Blocks Cell-Cycle Progression of Anchorage-Dependent Fibroblasts on Fibronectin through Inhibition of Syndecan-4", *Onogene*, vol. 23, No. 25, pp. 3917-3926 (2003).
Orlandi, Güssow, Jones and Winter, "Cloning Immunoglobulin Variable Domains for Expression by the Polymerase Chain Reaction", *Proc Natl Acad Sci USA*, vol. 86, No. 10, pp. 3833-3837 (1989).
Pesheva et al., "Tenascin-R (J1 160/180 Inhibits Fibronectin-Mediated Cell Adhesion—Functional Relatedness to Tenascin-C", *J Cell Sci*, vol. 7, Pt. 8, pp. 2323-2333 (1994).
Rapraeger, "Syndecan-Regulated Receptor Signaling", *J Cell Biol*, vol. 149, No. 5, pp. 995-997 (2000).
Redick, Settles, Briscoe and Erickson, "Defining Fibronectin's Cell Adhesion Synergy Site by Site-Directed Mutagenesis", *J Cell Biol*, vol. 149, No. 2, pp. 521-527 (2000).
Rovero, Quartara and Fabbri, "Solid-Phase Synthesis of Neurokinin A Antagonists", *Int J Peptide Protein Res*, vol. 37, No. 2, pp. 140-144 (1991).
Ruoslahti, "Integrins as Signaling Molecules and Targets for Tumor Therapy, " *Kidney Int*, vol. 51, No. 5, pp. 1413-1417 (1997).
Ruoslaht, "Fibronectin and Its Integrin Receptors in Cancer", *Adv Cancer Res*, vol. 76, pp. 1-20 (1999).
Salmivirta et al., "Syndecan from Embryonic Tooth Mesenchyme Binds Tenascin", *J Biol Chem*, vol. 266, No. 12, pp. 7733-7739 (1991).
Saoncella et al., "Syndecan-4 Signals Cooperatively with Integrins in A Rho-Dependent Manner in the Assembly of Focal Adhesions and Actin Stress Fibers", *Proc Natl Aced Sci USA*, vol. 96, No. 6, pp. 2805-2810 (1999).
Schreiner et al, "Isolation and Characterization of Chinese Hamster Ovary Cell Variants Deficient in the Expression of Fibronectin Receptor", *J Cell Biol*, vol. 109, No. 6, Pt. 1, pp. 3157-3167 (1989).
Schreiner, Fisher, Hussein and Juliano, "Increased Tumorigenicity of Fibronectin Receptor Deficient Chinese Hamster Ovary Cell Variants", *Cancer Res*, vol. 51, No. 6, pp. 1738-1740 (1991).
Schnapp et al., "The Human Integrin $\alpha 8\beta 1$ Functions as a Receptor for Tenascin, Fibronectin, and Vitronectin", *J Biol Chem*, vol. 270, No. 39, pp. 23196-23202 (1995).
Schnyder et al., "Distribution Pattern of Tenascin-C in Normal and Neoplastic Mesenchymal Tissues", Int J Cancer, vol. 72, No. 2, pp. 217-224 (1997).
Sharma et al., "Crystal Structure of a Heparin- and Integrin-Binding Segment of Human Fibronectin", *EMBO J*, vol. 18, No. 5, pp. 1468-1479 (1999).
Sriramarao, Mendler and Bourdon, "Endothelial Cell Attachment and Spreading on Human Tenascin is Mediated by $\alpha_2\beta_1$ and $\alpha_v\beta_3$ Integrins", *J Cell Sci*, vol. 105, Pt. 4, pp. 1001-1012 (1993).
Stoll et al., "The Extracellular Human Melanoma Inhibitory Activity (MIA) Protein Adopts an SH3 Domain-Like Fold", *EMBO J*, vol. 20, No. 3, pp. 340-349 (2001).
Talts et al., "Tenascin-C Modulates Tumor Stroma and Monocyte/Macrophage Recruitment but Not Tumor Growth or Metastasis in a Mouse Strain with Spontaneous Mammary Cancer", *J Cell Sci*, vol. 112, Pt. 12, pp. 1855-1864 (1999).

Tan et al., "Extracellular Matrix Regulates Steady-State mRNA Levels of the Proliferation Associated Protein Ki-67 in Endometrial Cancer Cells", *Cancer Lett*, vol. 140, Nos. 1-2, pp. 145-152 (1999).

Thomasset et al., "Expression of Autoactivated Stromelysin-1 in Mammary Glands of Transgenic Mice Leads to a Reactive Stroma During Early Development", *Am J Pathol*, vol. 153, No. 2, pp. 457-467 (1998).

Tumova, Woods and Couchman, "Heparan Sulfate Chains from Glypican and Syndecans Bind the Hep II Domain of Fibronectin Similarly Despite Minor Structural Differences", *J Biol Chem*, vol. 275, No. 13, pp. 9410-9417 (2000).

Vaughan, Huber, Chiquet and Winterhalter, "A Major, Six-Armed Glycoprotein from Embryonic Cartilage", *EMBO J*, vol. 6, No. 2, pp. 349-353 (1987).

Vaughan et al., "Tenascin-Contactin/F11 Interactions: A Clue for a Developmental Role?", *Perspect Dev Neurobiol*, vol. 2, No. 1, pp. 43-52 (1994).

Vollmer, "Biologic and Oncologic Implications of Tenascin-C/Hexabrachion Proteins", *Crit Rev Oncol Hematol*, vol. 25, No. 3, pp. 187-210 (1997).

Ward et al., "Binding Activities of a Repertoire of Single Immunoglobulin Variable Domains Secreted from *Escherichia coli*", *Nature*, vol. 341, No. 6242, pp. 544-546 (1989).

Winter and Milstein, "Man-Made Antibodies", *Nature*, vol. 349, No. 6307, pp. 293-299 (1991).

Woods and Couchman, "Syndecan 4 Heparan Sulfate Proteoglycan Is a Selectively Enriched and Widespread Focal Adhesion Component", *Mol Biol Cell*, vol. 5, No. 2, pp. 183-192 (1994).

Woods, Langley, Tumova and Couchman, "Syndecan-4 Binding to the High Affinity Heparin-Binding Domain of Fibronectin Drives Focal Adhesion Formation in Fibroblasts", *Arch Biochem Biophys*, vol. 374, No. 1, pp. 66-72 (2000).

Yokosaki et al., "The Integrin $\alpha 9\beta 1$ Mediates Cell Attachment to a Non-RGD Site in the Third Fibronectin Type III Repeat of Tenascin", *J Biol Chem*, vol. 269, No. 43, pp. 26691-26696 (1994).

Yokoyama, Erickson, Ikeda and Takada, "Identification of Amino Acid Sequences in Fibrinogen $\gamma$-Chain and Tenascin C C-Terminal Domains Critical for Binding to Integrin $\alpha_v\beta_3$", *J Biol Chem*, vol. 275, No. 22, pp. 16891-16896 (2000).

Zvibel et al., "Soluble and Matrix-Associated Heparan Sulfate Proteoglycans Increase Expression of ERB-B2 and ERB-B3 in Colon Cancer Cell Lines", *Int J Cancer*, vol. 91, No. 3, pp. 316-321 (2001).

Chung, et al., "Binding of Tenascin-C to Soluble Fibronectin and Matrix Fibrils", Jour. Biol. Chem., vol. 270, pp. 29012-29017 (1995).

Database WPI, Derwent Publications Ltd., No. XP002227588, (AN-365245) London, GB (1993).

International Pharmacopoeia Fourth Edition (http://www.who.int/phint/en/p/doctree/).

Material Safety Data Sheet for Sodium Azide (http://msds.chem.ox.ac.uk/SO/sodium_azide.html).

THAM—tromethamine injection, solution (http://dailymed.nlm.nih.gov/dailymed/fdaDrugXsl.cfm?id=1047&type=display).

\* cited by examiner

USE OF HEPARIN-BINDING DOMAIN OF FIBRONECTIN FOR DIAGNOSIS AND TREATMENT OF CANCER

CROSS REFERENCE TO RELATED APPLICATIONS

This application is a continuation of U.S. patent application Ser. No. 10/485,924, filed on Feb. 3, 2004, now abandoned, which application is a national phase application pursuant to 35U.S.C. §371 of PCT/EP02/08881, filed Aug. 8, 2002, which claims the benefit of United Kingdom Application No. 0119476.0, filed Aug. 9, 2001, the contents of each of which are incorporated herein by reference.

The present invention relates to active agents having anti-tumour and/or anti-tumourigenic activity, pharmaceutical compositions of these agents and the pharmaceutical uses of such agents and compositions. The invention also relates to in vitro methods of screening agents for anti-tumour and/or anti-tumourigenic activity.

Tenascin-C is an adhesion-modulatory extracellular matrix (ECM) molecule for a variety of cell types (reviewed in Vollmer, G. (1997) Crit Rev Oncol Hematol 25: 187-210). Tenascin-C is prominently expressed in the stroma of most solid tumours (Chiquet-Ehrismann, R. et al (1986) Cell 47: 131-139) and is found around newly formed blood vessels (Schnyder, B. et al (1997) Int J Cancer 72: 217-224). Tenascin-C expression precedes the manifestation of mammary neoplasia in stromelysin/MMP3 transgenic mice suggesting that tenascin-C might be involved in early steps of tumourigenesis (Thomasset, N. et al (1998) Am J Pathol 153: 457-467). Despite intriguing expression patterns the roles of tenascin-C in tumourigenesis and tumour progression are not known.

The ECM has an important regulatory function in tissue homeostasis and, together with oncogenes and tumour suppressor genes is critically involved in tumourigenesis (reviewed in Boudreau, N. & Bissell, M. J. (1998) Curr Opin Cell Biol 10: 640-646 and Ruoslahti, E. (1999) Adv Cancer Res 76: 1-20). Enforced interaction of tumour cells with fibronectin can block proliferation in cell culture and can decrease tumour growth in nude mice (Akamatsu H. et al (1996) Cancer Res 56: 4541-4546 and Giancotti, F. G & Ruoslahti, E. (1990) Cell 60: 849-859). Tenascin-C was shown to disrupt the interaction of cells with fibronectin and by that may enhance tumour cell proliferation. Chiquet-Ehrismann, R. et al (1988) Cell 53: 383-390 were the first to show that tenascin-C binds to fibronectin, blocks cell attachment to fibronectin and increases proliferation of rat breast adenocarcinoma cells (Chiquet-Ehrismann, R. et al (1986) Cell 47: 131-139). Tenascin-C binds fibronectin in an RGD-independent manner indicating that tenascin-C does not block the RGD cell binding site in fibronectin (Chiquet-Ehrismann, R. et al (1988) Cell 53: 383-390). The mechanism of how tenascin-C blocks cell attachment to fibronectin is not known.

Upon cell adhesion, signals from the ECM are coupled to the cytoskeleton through specific cell surface receptors (see the review by Hynes, R. O. (1999) Trends Cell Biol 9: M33-37). In particular, cell adhesion to fibronectin involving integrins and proteoglycans orchestrates an assembly of adhesion complexes and a rearrangement of the actin cytoskeleton, thereby triggering cytoplasmic signalling that determines cell behaviour, e.g. survival and proliferation (see the review by Giancotti, F. G. & Ruoslahti, E. (1990) Cell 60: 849-859).

Fibroblasts can attach on the cell binding site of fibronectin (RGD and synergy site) but, for full spreading including focal contact and actin stress fibre formation, additional activation of syndecan-4 is required (Woods, A. & Couchman, J. R. (1994) Mol Biol Cell 5: 183-192). Syndecan-4 is documented to be required for full cell spreading through interaction with the HepII site in fibronectin (Tumova, S. et al (2000) J Biol Chem 275: 9410-9417 and Saoncella, S. et al (1999) P.N.A.S. 95: 2805-2810). Cell binding of syndecan-4 was shown to be mediated through the heparin binding site II (HepII site) in fibronectin (Woods, A. et al (2000) Arch Biochem Biophys 374: 66-72) and upon clustering, syndecan-4 initiates cytoplasmic signalling involving integrins (see review by Rapraeger, A. C. (2000) J Cell Biol 149: 995-998).

Zvibel, I. et al (2001) Int J Cancer 91: 316-321 showed that the expression of growth promoting erb-B2 and erb-B3 is increased upon addition of soluble syndecan-4 to colon cancer cells.

Several integrins have been characterised as cell surface receptors for tenascin-C (Sriramarao, P. et al (1993) J Cell Sci 105: 1001-1012; Yokosaki, Y. et al (1994) J Biol Chem 269: 26691-26696; Schnapp, L. M. et al (1995) J Biol Chem 270: 23196-23202; and Yokoyama, K. et al (2000) J Biol Chem 275: 16891-16898). Tenascin-C has also been shown to bind to syndecan (Salmivirta, M. et al (1991) J Biol Chem 266: 7733-7739) and other sulphated glycosaminoglycans (Chiquet, M. & Fambrough, D. M. (1984) J Cell Biol 98: 1937-1946; Vaughan, L. et al (1987) EMBO J 6: 349-353; Barnea, G. et al (1994) J Biol Chem 269: 14349-14352; Grumet, M. et al (1994) J Biol Chem 269: 12142-12146; Milev, P. et al (1994) J Cell Biol 127: 1703-1715; Vaughan, L. et al (1994) Perspect Dev Neurobiol 2: 43-52; and Chung, C. Y. & Erikson, H. P. (1987) J Cell Sci 110: 1413-1419). Whether binding of tenascin-C to any of these receptors plays a role in tenascin-C-induced adhesion modulation on fibronectin affecting tumour cell proliferation is not known.

Blocking integrin function by competition mechanisms is an emerging topic in cell adhesion modulation. Examples are high molecular kininogen masking the $\alpha v\beta 3$ integrin binding site in vitronectin (Asakura, S. et al (1998) J Biochem (Tokyo) 124: 473-484) and the melanoma inhibitory activity (MIA) that appears to compete with $\alpha 4\beta 1$ integrin binding to the $14^{th}$ fibronectin type III repeat in fibronectin through its SH3 like domain (Stoll, R. et al (2001) EMBO J 20: 340-349).

Fibronectin is a large multidomain glycoprotein found in connective tissue, on cell surfaces, and in plasma and other body fluids. Fibronectin interacts with a variety of macromolecules including components of the cytoskeleton and the extracellular matrix, circulating components of the blood clotting, fibrinolytic, acute phase and complement systems, and with cell-surface receptors on a variety of cells including fibroblasts, neurons, phagocytes and bacteria. Fibronectin also interacts with itself, forming fibrillar entities whose structure is poorly understood.

The amino acid sequence of FN reveals three types of internally homologous repeats or modules, usually separated by short connecting sequences. There are twelve type I, two type II and fifteen type III modules, also referred to as FNI, FNII and FNIII. Each module constitutes an independently folded unit, often referred to as a domain, but not to be confused with "functional domains" that frequently contain more than one module. Modules homologous to those in fibronectin are also found in other proteins, especially the type III which is one of the most ubiquitous of all modules, being found in about 2% of animal proteins. Amino acid sequences of fibronectin modules are highly conserved. All three fibronectin modules contain several conserved core residues.

There are four sites of alternate splicing of fibronectin mRNA. Of these, the first two result in the insertion of extra type III domains (EDA and EDB) after modules III-11 and III-7 respectively. These modules are virtually absent from adult tissue but are differentially expressed during embryonic development and again in malignant or injured tissue and during angiogenesis. The extra EDA module renders fibronectin a better substrate for cell spreading and migration and has been used as a marker for certain types of cancer. No specific ligands have been identified for either of these domains.

Cell adhesion to fibronectin plays an important role in tumourigenesis and angiogenesis with an inverse correlation of tumourigenesis and adhesion of tumour cells to fibronectin (Akiyama, S. K. et al (1995) Cancer Metastasis Rev, 14: 173-189; and Ruoslahti, E. (1997) Kidney Int. 51: 1413-1417). In particular, blocking the α5β1 integrin enhances DNA replication (Gong, J. et al (1998) J Biol Chem 273: 1662-1669) and overexpression of integrin α5 β1 decreases proliferation and tumourigenesis of CHO cells in nude mice (Giancoiti, F. G. & Ruoslahti, E. (1990) Cell 60: 849-859; Gong, J. et al (1997) Cell Growth Differ 8: 83-90). Although the single animal model analysed does not support a tumourigenesis-enhancing effect of tenascin-C (Talts, J. F. et al (1999) J Cell Sci 112: 1855-1864), a wealth of immunohistochemical studies (Tan, M. I. et al (1999) Cancer Left 140: 145-152; and Jahkola, T. et al (1998) Eur J Cancer 34: 1687-1692) and cell culture experiments (Chiquet-Ehrismann, R. et al (1986) Cell 47: 131-139) suggest a role of tenascin-C in tumourigenesis especially by enhancing proliferation of cancer cells in situ.

U.S. Pat. No. 5,641,483 (Beaulieu) discloses topical gel and cream formulations containing human plasma fibronectin for the healing of cutaneous wounds. The formulations provide slow release and increased contact time of fibronectin to the wound site leading to effective absorption of an effective wound healing amount of fibronectin in the skin.

U.S. Pat. No. 5,958,874 (Clark et al) provides an extracellular matrix for wound healing comprising a recombinant fibronectin protein and a backbone matrix. The recombinant fibronectin protein comprises peptides from at least three fibronectin domains; the three fibronectin domains being the cell binding domain, the IIICS domain, and the heparin II binding domain.

U.S. Pat. No. 5,750,378 (Goodheart et al) teaches a method of producing cellular fibronectin in cell culture and then harvesting the fibronectin. One of the suggested uses of the cellular fibronectin is the treatment of cancer resections in human or veterinary medicine.

U.S. Pat. No. 6,060,317 (Malech) teaches a method of transducing mammalian cells, and products related thereto including contacting cells with a viral-vector in the presence of a multi-functional chemical moiety. A multifunctional chemical moiety has at least one cell-surface binding domain of e.g. fibronectin or tenascin linked to at least one virus binding domain, e.g. heparin II binding domain of fibronectin. One of the suggested uses of this method treatment of genetic deficiencies such as neoplasias.

U.S. Pat. No. 6,180,610 (Chen et al) concerns osteogenic compositions comprising a matrix, an osteoinductive factor (e.g. mineralized bone) and an extracellular matrix protein. In one claimed embodiment the extracellular matrix protein is fibronectin.

U.S. Pat. No. 6,025,150 (Livant) discloses a wound healing composition comprising a fibronectin-derived peptide containing the amino acid sequence PHSRN. U.S. Pat. No. 6,194,378 (Clark et al) discloses fibronectin peptides-based extracellular matrix for wound healing containing peptides from two or more fibronectin domains in a backbone matrix, e.g. containing cell-binding domain and heparin II binding domain.

WO 94 13692 A1 (Regents of the University of Minnesota et al) teaches a method for treating acute or chronic inflammatory or autoimmune disorders comprising administering a polypeptide having at least three amino acids corresponding to an amino acid sequence within the heparin-binding region of fibronectin or an RGD-containing amino acid sequence.

WO 00 55181 A1 (The General Hospital Corp.) concerns a method of modulating cell attachment and migration which includes administering an agent which modulates the interaction (binding) of the syndecan-4 ectodomain with a counterligand, e.g. the heparin-binding domain of an ECM. Examples for such agents are syndecan binding or cell binding domain of fibronectin, vitronectin, laminin, collagen, or a syndecan-4 binding portion of such an ECM molecule or any other peptide which binds to the ectodomain of syndecan-4.

WO 01 72776 A2 (Wisconsin Alumni Research Foundation) concerns a method for reducing cell contacts and matrix organization in trabecular meshwork of a human or nonhuman eye is disclosed which includes the step of administering a suitable peptide having a sequence found in the Hep II domain of fibronectin where the peptide has an ability to disrupt cell contacts and matrix formation. In particular, a pentapeptide (PRARI) of the FNIII 14 is disclosed which binds syndecan. FNIII14 is disclosed to be the most active region of the Hep II domain.

EP 0399 806 (Takara Shuzo Co Ltd) discloses a functional polypeptide which has the cell binding domain of human fibronectin bound directly or by means of a linker amino acid or peptide with the heparin-binding domain of human fibronectin which has not been identified in detail but is believed to consist of three type III repeating sequences which are made of about 90 amino acids each. Disclosed is also a method for its preparation and the use of such functional polypeptide to inhibit angiogenesis EP 0 837 074 A2 (Hisamitsu Pharmaceutical Co Inc) teaches fibronectin peptides of 30 amino acids or less comprising the amino acid sequence YTIYVIAL and having cell adhesion inhibition activity. Such peptides fall within the FNIII-14 domain of fibronectin and are suggested for use in the treatment of a variety of diseases or conditions including inter alia cancer, rheumatism, asthma, allergic disease, thrombosis, transplant rejection, wound healing, inflammation, immunological inflammation containing enteritis nephrocalcinosis (such as colitis ulcerosa), and autoimmune disease.

The present inventors have investigated cell adhesion and proliferation of tumour cells and discovered that tenascin-C blocks cell attachment and spreading on fibronectin by specific binding to the 13th fibronectin type III repeat (FNIII13) (SEQ ID NO:1) of the HepII site, thereby interfering with syndecan-4 binding to fibronectin. This has been found to correlate with an enhanced proliferation of tumour cells that can be neutralised by recombinant FNIII13. The inventors have also discovered that tenascin-C competes with binding of syndecan-4 to the HepII site in fibronectin, thereby blocking or altering syndecan-4 function. This prevents fibronectin adhesion signalling (observed as compromised cell attachment and spreading, lack of fibronectin specific cell adhesion structures, lack of actin stress fibres and increased proliferation of tumour cells on fibronectin). Overexpression of syndecan-4 as well as addition of FNIII13 or of a smaller peptide of FNIII 13 has been discovered to restore tenascin-C-compromised cell spreading. The inventors conclude that FNIII13 in fibronectin serves as a ligand for syndecan-4.

In summary, the inventors have discovered that tenascin-C blocks fibronectin specific adhesion signalling by masking the syndecan-4 binding site in fibronectin through direct interaction with FNIII13 in fibronectin. In consequence, interference with syndecan-4 function triggered enhanced proliferation of tumour cells by tenascin-C. The inventors have therefore discovered that tenascin-C impairs the adhesive function of fibronectin through blocking the co-receptor function of syndecan-4 in integrin signalling, thereby triggering tumour cell proliferation.

Accordingly, the present invention provides a composition for the prevention or prophylactic treatment of tumourigenesis or the treatment or prophylactic treatment of tumours or of any one or more of rheumatism, asthma, allergic diseases, autoimmune diseases, prevention of transplant rejection or the treatment or prophylactic treatment of any disease or condition involving tenascin/fibronectin interactions, e.g., thrombosis and atherosclerosis comprising a fragment of fibronectin having the heparin binding site II (HepII site).

The present invention also provides a composition for the prevention or prophylactic treatment of tumourigenesis or the treatment or prophylactic treatment of tumours or cancer or of any one or more of rheumatism, asthma, allergic diseases, autoimmune diseases, prevention of transplant rejection, thrombosis, atherosclerosis, or the treatment or prophylactic treatment of any disease or condition dependent on the interaction of tenascin with fibronectin comprising a fragment of fibronectin having all or a portion of the $13^{th}$ type III repeat (FNIII13) (SEQ ID NO:1) of fibronectin, wherein said portion interferes with tenascin binding to fibronectin. In a preferred embodiment the invention provides a composition comprising a portion of the FNIII13 fibronectin fragment, wherein said portion comprises the first five amino acids of the amino acid sequence set forth in SEQ ID NO: 3, wherein Xaa is any amino acid. Preferably, Xaa is a hydrophibic amino acid. In a more preferred embodiment the invention provides a composition comprising a portion of the FNIII13 fibronectin fragment, wherein the portion comprises the amino acid sequence set forth in SEQ ID NO: 3. Preferably, Xaa of the amino acid number 3, 5, 8, 13, 15, and 17 of SEQ ID NO:3 is a hydrophobic amino acid, Xaa of the amino acid number 7 and 10 of SEQ ID NO:3 is a charged amino acid, and Xaa of the amino acid number 6, 9, 11, 12, 14, 16, and 19 of SEQ ID NO:3 is a neutral amino acid (most preferably with a hydroxy group). In a most preferred embodiment the invention provides a composition comprising a portion of the FNIII13 fibronectin fragment, wherein said portion is a polypeptide having the amino acid sequence set forth in SEQ ID NO:4 or a variant thereof. Preferably, the invention provides a fragment comprising the first ten amino acids of the amino acid sequence set forth in SEQ ID NO:4. In another embodiment the invention provides a composition comprising a portion of the FNIII13 fibronectin fragment, wherein said portion is a polypeptide having the amino acid sequence set forth in SEQ ID NO:2 or a fragment or variant thereof. Preferably, the invention provides a composition comprising a portion of a FNIII13 fibronectin fragment as hereinabove described, wherein said portion is free of any other fibronectin domain or module. All of the hereinbefore described portions are portions which are capable of interfering with tenascin binding to fibronectin and which are capable of restoring a cell spreading defect imposed by tenascin.

The compositions of the invention are also useful for the treatment in wound healing. In particular, the invention provides a composition for wound healing comprising a fragment of fibronectin having all or a portion of the $13^{th}$ fibronectin type III repeat (FNIII13) free of any other fibronectin modules or domains. In another embodiment the invention provides a composition for wound healing comprising a portion of a fibronectin fragment, wherein said portion comprises the first five amino acids of the amino acid sequence set forth in SEQ ID NO: 3, wherein Xaa is any amino acid, free of any other fibronectin modules or domains. In yet another embodiment the invention provides a composition for wound healing comprising a portion of a fibronectin fragment, wherein said portion comprises the amino acid sequence set forth in SEQ ID NO: 3 or a fragment or variant thereof, wherein Xaa is any amino acid, free of any other fibronectin modules or domains. In yet another embodiment the invention provides a composition for wound healing comprising a portion of a fibronectin fragment, wherein said portion is a polypeptide having the amino acid sequence set forth in SEQ ID NO:4 or in SEQ ID NO: 2 or a fragment or variant thereof, free of any other fibronectin modules or domains.

The fibronectin fragments of the compositions of the invention may be the same or different, that is to say the compositions may comprise one or more species of fragment. Although the HepII site of fibronectin comprises FNIII12, FNIII13 and FNIII14, preferred fragments comprise just all or a portion of the 13th fibronectin type III repeat (FNIII13). Thus, a fibronectin fragment includes any polypeptide (i.e. protein) species of fibronectin that has fewer amino acids than the native whole fibronectin. In other words, fibronectin fragments may fall within the range 5 to n−1 amino acid residues, wherein n is the full length, native fibronectin. In preferred embodiments, a fibronectin fragment is FNIII13 (SEQ ID NO:1), or a portion or a variant thereof, preferably free of any other fibronectin domains.

"Fragments" and "portion" of fragments as small as 5 amino acid residues are within the scope of the invention. In a preferred embodiment the fibronectin fragments of the compositions of the invention comprise the amino acid sequence Arg 98 to Arg 146 according to the numbering used in Sharma et al EMBO J 18: 1468-1479. This fragment comprising amino acids 98 to 146 can restore compromised fibronectin adhesion signalling induced by tenascin-C. The peptide is shown in SEQ ID NO 2.

A particularly preferred fragment is the fragment of SEQ ID NO:4 although larger or smaller fragments may be used. The fragments and portion of fragments may fall in the range 5 to 100 amino acid residues, preferably having 89, more preferably having 49, even more preferably having at least 5 or 6, even more preferably having at least 10, most preferably having at least 20 amino acid residues. Other properties of the peptide (such as solubility) may govern the actual length of peptide used. In one embodiment the invention provides a fragment of fibronectin having all or a portion of the 89 amino acids of the sequence of the FNIII 13 fragment (SEQ ID NO:1). In another embodiment the invention provides a fragment of fibronectin having all or a portion of the 49 amino acids of the sequence as set forth in SEQ ID NO:2, or having all or a portion of the 20 amino acids of the sequence as set forth in SEQ ID NO:3 or SEQ ID NO:4. In an alternative embodiment the invention provides a portion of fragment having the first five amino acids of SEQ ID NO:3 or SEQ ID NO:4. In another embodiment the invention provides a portion of fragment having the first six amino acids of SEQ ID NO:3 or SEQ ID NO:4. Preferably, the invention provides a portion of fragment having the first ten amino acids of the amino acid sequence set forth in SEQ ID NO:3 or SEQ ID NO:4. Xaa in SEQ ID NO:3 may be any amino acid, preferably an amino acid as hereinbefore described.

The compositions of the invention may also include other individual fibronectin fragments in addition to those that are or comprise the HepI site or the FNIII13 domain or portion thereof. These other fragments may be selected from FNIII13 to FNIII12, FNIII14 and FNIII15, CS or the HepI site, or fragments thereof, for example. The other preferred fragments also include FNII4, FNIII5 and FNIII6, including contiguous fragments comprising two or more of these domains, or fragments thereof. In preferred embodiments, the fibronectin fragments of the compositions of the invention are free of other fibronectin sequences or domains. In these circumstances, the compositions of the invention can include other proteins, peptides or fragments from proteins other than fibronectin.

The invention therefore provides pharmaceutical compositions for humans or veterinary compositions for animal use that comprise one or more of the aforementioned active fragments of fibronectin. The compositions may also include other active or non-active agents. Non-active agents may include a pharmaceutically acceptable excipient, diluent or carrier, but not limited to saline, buffered saline, dextrose and water.

The fibronectin fragment is preferably one which is capable of restoring a cell spreading defect imposed by tenascin such as restoring syndecan signalling although there may be other potential targets. Syndecan signalling manifests itself in the way in which cells spread when cultured in vitro. Instead of a rounded morphology the cells adopt a flattened, and stretched appearance visible under the light microscope. The quality of spreading which is restored can be determined by observation or measured by morphometric analysis (determining the surface area of the cell attached to the substrate). Other manifestations of syndecan signalling include the restored adhesion of cells to fibronectin in vitro, the presence of specific cell adhesion structures and actin stress fibres.

Various approaches and practical methods of measuring syndecan signalling are described hereinafter.

There are a number of syndecan molecules, including syndecan 1, syndecan 2, syndecan 3 and syndecan 4. Preferred compositions of the invention restore syndecan 4-mediated signalling.

In preferred embodiments the fibronectin fragment binds to tenascin; preferably the tenascin binds to the HepII site of the fibronectin fragment, more preferably the tenascin binds to the FNIII13 site or portion thereof of the fibronectin fragment, or even more preferably the tenascin binds to the peptide (6-25) (SEQ ID NO:4) of the FNIII 13 site, or to any portion of a fibronectin fragment as hereinbefore described, preferably to the portion of fragment having the first ten amino acids of the amino acid sequence set forth in SEQ ID NO:4. In particularly preferred embodiments the tenascin is tenascin C, although in other embodiments the tenascin may be tenascin X or tenascin Y, R or W.

In particularly preferred embodiments heparin competes with syndecan for binding to the HepII site of the fibronectin fragment, or for binding to the FNIII13 site or portion thereof of the fibronectin fragment. In a more particularly preferred embodiments the portion of a fibronectin fragment of the invention competes with the FNIII13 site or portion thereof of the native fibronectin protein for tenascin binding.

In a particularly preferred embodiment tenascin binds to the heparin binding site(s) of FNIII13 or FNIII13 fragments of the invention.

The invention also provides compositions wherein the fibronectin fragment(s) are produced by recombinant means. In so doing, the fragment(s) may be engineered so that the HepII site or FNIII13 site or portion thereof is present but that the flanking sequences of the remainder of the fibronectin fragment can comprise amino acid sequence that the skilled person may find beneficial in other practical respects, e.g. stability, solubility, or the possession of some additional biological function, e.g. cell binding activity via integrin binding sites. Such variant fragments made by recombinant means familiar to one of skill in the art comprise a fibronectin fragment having the 13th fibronectin type III repeat (FNIII13), or a portion or variant of the invention as hereinabove described, and any one or more of the other fibronectin domains or portions thereof, or other proteins, peptides or fragments from proteins other than fibronectin.

The complete nucleotide sequence of fibronectin is provided in U.S. Pat. No. 5,679,230. The amino acid sequence is provided in Kornblihtt et al EMBO J 4: 1755-1759.

Also included within the invention are variants and derivatives of the fibronectin fragment, whether produced by recombinant means or synthetic means or isolated from naturally occurring sources. For example, peptides having modified amino acids/peptide linkages, and peptides containing non-naturally occurring amino acids and/or cyclic peptides, which may have improved properties such as stability or activity are included. In addition the peptides of the invention may be in the form of a fusion with another protein, for example, tags for the targeted delivery or detection of the HepII site or the FNIII13 fragments or portions or variants thereof.

A "variant" in terms of amino acid sequence defines an amino acid sequence that differs by one or more amino acids from another, usually related amino acid sequence. The variant may have "conservative" changes, wherein a substituted amino acid has similar structural or chemical properties (e.g. replacement of leucine with isoleucine). Less likely, a variant may have "non-conservative" changes, e.g. replacement of a glycine with a tryptophan. Similar minor variations may also include amino acid deletions or insertions (i.e. additions), or both. Guidance in determining which and how many amino acid residues may be substituted, inserted or deleted without abolishing activity may be found using computer programs well known in the art.

The present invention therefore provides a fragment of fibronectin as hereinbefore described having the heparin II binding site (HepII site) for use as a pharmaceutical. The present invention also provides a fragment of fibronectin as hereinbefore described having the 13$^{th}$ fibronectin type III repeat (FNIII13) or a portion or variant thereof, wherein said portion interferes with tenascin binding to fibronectin, for use as a pharmaceutical. The present invention also provides a portion of fragment of fibronectin for use as a pharmaceutical, wherein the portion has any one or more of the features as hereinbefore described.

The present invention further provides the use of a fragment of fibronectin as hereinbefore described having the heparin binding site II (HepII site), or having all or a portion of the 13$^{th}$ type III repeat (FNIII13), or having all or a portion of the peptide having the amino acid sequence as set forth in any one or more of the sequences of SEQ ID NOS:2 to 4 or fragments or variants thereof as hereinbefore described, for the manufacture of a medicament for the prevention or prophylactic treatment of tumourigenesis or the treatment or prophylactic treatment of tumours or cancer. The invention also includes the use of the fibronectin fragments of the invention for the manufacture of a medicament for the treatment or prophylactic treatment of any one or more of an immune related disease, including without limitation rheumatism, asthma, allergic diseases, autoimmune diseases, transplant rejection. The invention further includes the use of the fibronectin fragments of the invention for the manufacture of a medicament for the treatment or prophylactic treatment of any one or more of thrombosis, artherosclerosis, wound healing and any other disease or condition dependent on the interaction of tenascin with fibronectin.

The compositions and medicaments of the invention may therefore be used prophylactically in order to prevent tumours from forming, or they may be used in a curative or partly curative way to treat or contain a pre-existing tumourous condition. As well as tumours, cancerous or malignant conditions may be prevented or treated with compositions or medicaments of the invention.

The tumours or tumour cells are preferably those which express tenascin in the stroma, more preferably tenascin C. The expression of tenascin is preferably at least two-fold greater than non-tumour tissue or cells. In particularly preferred embodiments the tumours are solid tumours, e.g. mesenchymal tumours such as glioblastoma or epithelial cancers such as glioblastoma or breast carcinoma.

The invention also provides a method of preventing or prophylactic treatment of tumourigenesis or of treatment or prophylactic treatment of tumours or cancer or of any one or more of rheumatism, asthma, allergic diseases, autoimmune diseases, prevention of transplant rejection, thrombosis, atherosclerosis or the treatment or prophylactic treatment of any disease or condition dependent on the interaction of tenascin with fibronectin in an individual comprising administering an effective amount of a fibronectin fragment having all or a portion of the $13^{th}$ type III repeat (FNIII13), or having all or a portion of the peptide having the amino acid sequence as set forth in any one or more of the sequences of SEQ ID NOS:2 to 4 or a portion or variant of the invention.

The invention further provides a method of wound healing comprising administering an effective amount of the fibronectin fragments of the invention.

The determination of an effective dose is well within the capability of those skilled in the art. For any compound, the therapeutically effective dose can be estimated initially either in cell culture assays or in an appropriate animal model. The animal model is also used to achieve a desirable concentration range and route of administration. Such information can then be used to determine useful doses and routes for administration in humans.

A therapeutically effective dose refers to that amount of active agent which ameliorates the symptoms or condition. Therapeutic efficacy and toxicity of such compounds can be determined by standard pharmaceutical procedures in cell cultures or experimental animals (e.g., $ED_{50}$, the dose therapeutically effective in 50% of the population; and $LD_{50}$, the dose lethal to 50% of the population). The dose ratio between therapeutic and toxic effects is the therapeutic index, and it can be expressed as the ratio, $LD_{50}/ED_{50}$. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage may be chosen by the individual physician in view of the patient to be treated. Dosage and administration can be adjusted to provide sufficient levels of the active moiety or to maintain the desired effect. Additional factors which may be taken into account include the severity of the disease state (e.g. tumour size and location); age, weight and gender of the patient; diet; time and frequency of administration; drug combination(s); reaction sensitivities; and tolerance/response to therapy. Long acting pharmaceutical compositions can be administered on a daily basis, every 3 to 4 days, every week, or once every two weeks, depending on half-life and clearance rate of the particular formulation.

The invention further provides an antibody specifically reactive against a fragment of fibronectin as hereinbefore described having all or a portion of the $13^{th}$ type III repeat (FNIII13). The antibody may be monoclonal or polyclonal. Methods of producing polyclonal and monoclonal antibodies are known to those of skill in the art and described in the scientific and patent literature, see, e.g., Coligan, Current Protocols in Immunology, Wiley/Green, NY (1991); Stites (eds.) Basic and Clinical Immunology (7th ed.) Lange Medical Publications, Los Altos, Calif., and references cited therein (Stites); Goding, Monoclonal Antibodies: Principles and Practice (2nd ed.) Academic Press, New York, N.Y. (1986); and Kohler (1975) Nature 256: 495. Such techniques include selection of antibodies from libraries of recombinant antibodies displayed in phage or similar on cells. See, Huse (1989) Science 246: 1275 and Ward (1989) Nature 341: 544. Recombinant antibodies can be expressed by transient or stable expression vectors in mammalian cells, as in Norderhaug (1997) J. Immunol. Methods 204: 77-87.

The invention also provides other useful aspects including a method for identifying agents for the treatment or prophylactic treatment of tumourigenesis or cancer comprising contacting a test compound with cells exposed to ECM, fibronectin, FNIII13 fragment or a portion thereof and caused to proliferate by the presence of tenascin or a fragment thereof and then measuring one or more of:

a) cell proliferation;
    b) DNA synthesis;
    c) cell adhesion;
    d) cell spreading;
    e) focal adhesion and actin stress fibre formation on fibronectin;
    f) the proportion of cells entering S-phase of the cell cycle; and
    g) the binding of cells to extracellular matrix (ECM), preferably wherein the ECM is or comprises fibronectin; or
    h) any other output from the syndecan signalling pathway.

Although the hereinabove described method teaches a method for identifying agents for the treatment or prophylactic treatment of tumourigenesis or cancer, the method may also include identifying agents for the treatment or prophylactic treatment of any disease or condition dependent on the interaction of tenascin with fibronectin, which include without limitation rheumatism, asthma, allergic diseases, autoimmune diseases, transplant rejection, thrombosis, atherosclerosis, and/or wound healing.

The proliferating cells may be encouraged to proliferate by the addition of tenascin to the cell culture, preferably by coating the solid substrate therewith. The cell cultures are preferably grown on a solid substrate or in a liquid medium. A first measurement of one or more of (a) to (h) may be made prior to contacting the cells with a test compound. A second measurement may be made thereafter. A multiplicity of further measurements may be made over a period of hours or days after contact of the cells with the test compound. In this way a time course of the cellular response(s) may be obtained and analysed.

In preferred aspects one or more of the following arising after contacting cells with a test compound may indicate an anti-proliferative or anti-tumour agent:
    (a) a reduction in cell proliferation;
    (b) a reduction in DNA synthesis;

(c) an increase in cell adhesion, preferably to fibronectin;
(d) an increase in cell spreading;
(e) an increase in focal adhesion and actin stress fibre formation on fibronectin;
(f) a decrease in the proportion of cells entering S-phase of the cell cycle;
(g) an increase in the binding of cells to ECM, preferably fibronectin, FNII13 or a portion thereof; and
(h) an increase in any other output from the syndecan signalling pathway.

Any adhesive cell may be used in performing the method, including both normal and transformed cells. Such cells may be fibroblasts, epithelial cells, neuronal cells, endothelial cells, smooth muscle cells and astrocytes, for example.

Actin stress fibre formation may be assayed according to the Actin Assembly Assay described in Bloom, L et al (1999) Mol Biol Cell 10: 1521-1536. Adhesion assays may be performed according to the method described in Bloom, L et al (1999) or as described in the Examples below.

In preferred methods the cells express syndecan, in particular syndecan 4 and are grown in the presence of fibronectin and tenascin whether before, during or after contact with the test compound.

In other embodiments, the method of the invention may further comprise control cells grown in the absence of test compound and (a), (b), (c), (d), (e), (f), (g) and/or (h) are measured in both control and test cultures. The test measurements can thereby be normalised with respect to the control.

In another aspect the invention provides a method for the identification of potential anti-tumour or anti-tumourigenic compounds or compounds for the treatment or prophylactic treatment of any one or more of rheumatism, asthma, allergic diseases, autoimmune diseases, prevention of transplant rejection or the treatment or prophylactic treatment of any disease or condition dependent on the interaction of tenascin with fibronectins, e.g., thrombosis, wound healing and atherosclerosis in accordance with the invention comprising contacting a test compound with a system comprising:
(i) a fibronectin molecule, FNII13, or a portion or variant thereof, and
(ii) tenascin or a portion thereof capable of binding (i);
and then measuring the binding of (i) and (ii).

This method as hereinabove described provides an essentially cell-free system for the identification of potential anti-tumour or tumour preventing agents. The fibronectin molecule, portion, variant or fragment thereof is preferably FNII3, or a portion, variant or fragment thereof that is sufficient to permit measurable binding of tenascin thereto. This method relies on the ability of a potential anti-tumour agent to prevent, inhibit or disrupt the binding between fibronectin and tenascin. The nature of any disruption of the fibronectin and tenascin binding may be determined by the person of ordinary skill by performing a binding assay for fibronectin and tenascin. The relative amounts or concentrations of reagents and test compound may be varied, thereby permitting calculation of inhibition constants and other parameters, e.g. binding affinities. The optimisation of assay conditions will be well within the realm of one of ordinary skill in the art.

The system may further comprise a control without test compound and the binding of (i) and (ii) is measured in that control, thereby permitting corresponding measurements in the test system to be normalised relative to the control.

Another screening method for identifying agents effective against any disease or condition dependent on the interaction of tenascin with fibronectin comprises contacting a test compound with a system comprising:

(i) a fibronectin molecule, in particular FNII13, a portion or variant thereof,
(ii) a tenascin molecule or portion thereof capable of binding (i), and/or
(iii) a syndecan molecule capable of binding (i);
and then measuring the binding of (i) and (ii) and/or the binding of (i) and (iii).

In this way the potential of a test compound to be able to disrupt, inhibit or prevent tenascin binding to fibronectin may be correlated with its potential to restore syndecan binding to fibronectin. A decrease in the binding of (i) and (ii) correlates with an anti-proliferative or anti-tumour agent and an increase in the binding of (i) and (iii) correlates with an anti-proliferative or anti-tumour agent As with the previous screening aspect of the invention, this system may further comprise a control without test compound and the binding of (i) and (ii) and/or the binding of (i) and (iii) is measured.

A disease or condition dependent on the interaction of tenascin with fibronectin may include without limitation tumourigenesis or cancer, rheumatism, asthma, allergic diseases, autoimmune diseases, transplant rejection, thrombosis, atherosclerosis, and/or wound healing. In a preferred embodiment, the present invention provides agents which are effective against tumourigenesis or cancer, preferably anti-tumour or anti-proliferative agents.

In all of the aforementioned screening aspects of the invention the fibronectin molecule, portion or variant thereof may be selected from:
(a) intact fibronectin,
(b) FNIII13,
(c) a fragment of FNIII13 of at least 5 amino acid residues, or
(d) a fragment of fibronectin comprising the amino acid sequence as set forth in SEQ ID NO:2, SEQ ID NO:3 or SEQ ID NO:4 or a portion or variant thereof.

In any of aforementioned methods of the invention the tenascin is preferably intact tenascin, more preferably tenascin C. Also, the syndecan molecule preferably comprises the ectodomain of a syndecan, more preferably that of syndecan 4 (see McFall and Rapraeger (1998) J. Biol. Chem. 273: 28270-28276). However, active fragments or portion of fragments of these molecules may be employed.

One of the fibronectin molecule, portion or variant thereof, tenascin or syndecan or active fragments or portions thereof may be attached to a solid phase. The solid phase may comprise particles or be a surface. For example, particles such as latex beads or cellulose may be used. Examples of solid substrates include membrane filters, e.g. nitrocellulose, or polystyrene, e.g. in the form of a microtiter plate.

Where one component of the assay (screening) systems of the invention is coupled to a solid particle or substrate, then one or more of the other components not so coupled may be labelled. Examples of labels include radiolabels e.g. $^{14}C$ or $^{3}H$, dyes, metal sols, enzymes or biotin/avidin. By attaching such labels to "free" components in the system any binding assay may be carried out in solution in accordance with procedures well known in the art. After allowing the components to react solid phase particles can be separated from solution, e.g. by filtration or sedimentation (including centrifugation). In some embodiments immunoprecipitation may be used to separate bound and free labelled components. Usually, an antibody may be employed to bring an unlabelled component out of solution (whether or not this component has bound to another labelled component or not). After separation, the label present in solution (free) and the label present in or on the solid phase (bound) may be measured. Standard analyses of such bound and free data, e.g. Scatchard plots and the determination of affinity and inhibition constants for binding are well known to the person of ordinary skill in the art.

Where the solid phase is not particulate, e.g. in the form of a surface, such as a microtiter plate well, then binding assays measuring bound and free label may be performed but this will normally involve the removal of liquid phase from the wells after binding reactions have occurred. Advantageously, this assay format may dispense with the need for providing specifically labelled reaction components. Instead, labelled antibodies may be used to measure the binding of previously free reaction components to solid phase components.

In some embodiments the fibronectin molecule, variant or fragment thereof may be attached directly to a solid phase. In preferred immunoassay embodiments of this type, tenascin bound to fibronectin is measured using an antibody reactive against tenascin. The assays may also be performed in the presence of syndecan.

In other embodiments tenascin may be attached to a solid phase. In preferred immunoassay embodiments of this type, fibronectin molecule, variant or fragment thereof bound to tenascin is measured using an antibody reactive against fibronectin. The assays may also be performed in the presence of syndecan.

In further embodiments, syndecan may be attached to a solid phase and the binding assay with fibronectin molecule, variant or fragment thereof performed in the presence of tenascin. In preferred immunoassay embodiments of this type, fibronectin molecule, variant or fragment thereof bound to syndecan is measured using an antibody reactive against fibronectin.

Immunological binding assays are known in the art. For a review, see Methods in Cell Biology Vol. 37: Antibodies in Cell Biology, Asai, (Ed.) Academic Press, Inc. New York (1993).

A label may be any detectable composition whereby the detection can be spectroscopic, photochemical, biochemical, immunochemical, physical or chemical. For example, useful labels can include $^{32}P$, $^{35}S$, $^{3}H$, $^{14}C$, $^{125}I$, $^{131}I$, fluorescent dyes (e.g. FITC, rhodamine and lanthanide phosphors), electron-dense reagents, enzymes, e.g. as commonly used in ELISA (e.g. horseradish peroxidase, beta-galactosidase, luciferase and alkaline phosphatase), biotin, dioxigenin, or haptens and proteins for which antisera or monoclonal antibodies are available. The label may be directly incorporated into a target compound to be detected, or it may be attached to a probe or antibody which binds to the target.

Throughout the assays of the invention, incubation and/or washing steps may be required after each application of reagent or incubation of combinations of reagents. Incubation steps may vary from about 5 minutes to several hours, perhaps from about 30 minutes to about 6 hours. However, the incubation time usually depends upon the assay format, analyte, volume of solution, concentrations, and so forth. Usually, the assays should be carried out at ambient temperature, although they may be conducted at temperatures; in the range 10° C. to 40° C., for example.

A particularly preferred assay format is an enzyme-linked immunosorbent assay (ELISA).

All of the aforementioned methods of screening of the invention are equally applicable to the screening of substances for biological activity and potential agents for wound healing or treatment of artherosclerosis, or for the treatment or prophylactic treatment of any disease or condition dependent on the interaction of tenascin with fibronectin.

Also included within the scope of the present invention are anti-tumourigenic, anti-tumour, anti-metastatic, wound healing or anti-artherosclerosis substances or substances for the treatment or prophylactic treatment of any one or more of rheumatism, asthma, allergic disease, autoimmune disease, prevention of transplant rejection or for the treatment or prophylactic treatment of any disease or condition dependent on the interaction of tenascin with fibronectin, e.g thrombosis, identified by any of the screening methods of the invention. These substances may be proteins, polypeptides or small organic molecules (drugs). The invention therefore includes pharmaceutical compositions for preventing or treating tumours, metastasis, wound healing or artherosclerosis and comprising one or more of the substances identified by a method of the invention.

The present invention also provides a method of diagnosing or prognosing cancer comprising:
  a) obtaining a sample from an individual;
  b) analysing said sample for the presence of accessible FNIII13 or a portion or variant thereof; and
  c) correlating the presence of accessible FNIII13 or a portion or variant thereof with a favourable prognosis or diagnosis.

Accessible FNIII13 or a portion or variant thereof may be detected using an antibody specific for FNIII13 or a fragment thereof, and a control assay can be carried out using an antibody specific for a different area of fibronectin. The sample is preferably a tissue sample mounted onto a solid surface for histochemical analysis. The presence of detectable, accessible FNIII13 or a portion or variant thereof indicates that FNIII13 is accessible to cells for binding. In particular, if an FNIII13-specific antibody reacts with FNIII13 in a tissue section, then there is an expectation that cells will also be able to interact with FNIII13 in that sample. This leads to a favourable diagnosis or prognosis. If, on the other hand, the antibody does not react with FNIII13 in the tissue section, e.g. because tenascin is masking the FNIII13 site, then there is an expectation that cells cannot interact. This leads to an unfavourable diagnosis or prognosis.

In a preferred embodiment, the invention provides kits suitable for use in the diagnostic or prognostic methods of the invention. Such kits comprise reagents useful for carrying out these methods, for example, antibodies from one or more species specific for FNIII13. Additionally, kits can contain antibodies from one or more species specific for other parts of the fibronectin molecule, for use as a control. Secondary antibodies that recognise either or both such primary anti-fibronectin antibodies can also be included for the purpose of recognition and detection of primary antibody binding to a sample. Such secondary antibodies can be labelled for detection e.g. with fluorophores, enzymes, radioactive labels or otherwise. Other detection labels will occur to those skilled in the art. Alternatively, the primary anti-fibronectin antibodies can be labelled for direction detection.

Methods for the production of polyclonal and monoclonal antibodies are known to those of skill in the art. In brief, an immunogen is mixed with a suitable adjuvant and animals are immunised. The immune response to the immunogen preparation is monitored by taking test bleeds and determining the titer of reactivity to the immunogen. When appropriately high titers of antibody to the immunogen are obtained, blood is collected from the animal and antisera are prepared. The antisera may be further fractionated to enrich for the reactive species of antibodies.

Monoclonal antibodies to fibronectin molecule, variant or fragment thereof, tenascin or syndecan may be prepared using any technique which provides for the production of antibody molecules by continuous cell lines in culture. These include but are not limited to the hybridoma technique originally described by Koehler and Milstein (Koehler and Milstein (1975) Nature 256: 495-497), the human B-cell hybridoma technique (Kosbor et al (1983) Immunol Today 4: 72; Cote et al (1983) Proc Natl Acad Sci 80: 2026-2030) and the EBV-hybridoma technique (Cole et al (1985) Monoclonal Antibodies and Cancer Therapy, Alan R Liss Inc, New York N.Y., pp 77-96). Large amounts of monoclonal antibodies for use in immunoassays may be obtained by various techniques familiar to those skilled in the art. Briefly, spleen cells from an animal immunised with the desired protein are immortalised, commonly by fusion with a myeloma cell. Alternative methods of immortalisation include transformation with Epstein Barr Virus, oncogenes, or retroviruses, or other methods well known in the art. Colonies arising from single immortalised cells are screened for production of antibodies of the desired specificity and affinity for fibronectin molecule, variant or fragment thereof, tenascin or syndecan. The yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from appropriate human B cells, i.e. immunised according to a general protocol.

For the production of antibodies, various hosts including goats, rabbits, rats, mice, etc may be immunised by injection with fibronectin molecule, variant or fragment thereof, tenascin or syndecan or any portion or fragment that retains immunogenic properties. Depending on the host species, various adjuvants may be used to increase immunological response. Such adjuvants are commercially available, and include but are not limited to Freund's, mineral gels such as aluminium hydroxide, and surface active substances such as lysolecithin, pluronic polyols, polyanions, peptides, oil emulsions, keyhole limpet hemocyanin, and dinitrophenol. BCG (Bacillus Calmette-Guerin) and *Corynebacterium parvum* are potentially useful adjuvants.

Animals (e.g. inbred strain of mice or rabbits) can be immunised with immunogen using a standard adjuvant, such as Freund's adjuvant, and a standard immunisation protocol. Alternatively, a synthetic peptide conjugated to a carrier protein can be used an immunogen. Polyclonal sera are collected and titered against the immunogen in an immunoassay, for example, a solid phase immunoassay with the immunogen immobilised on a solid support. Polyclonal antisera with a titer of, for example, $10^4$ or greater are selected and tested for their cross-reactivity against homologous proteins from other organisms and/or non-immunogen protein, using, for example, a competitive binding immunoassay. Specific monoclonal and polyclonal antibodies and antisera will usually bind with a $K_D$ of at least about 1 µM, preferably at least about 0.1 µM or better, and most preferably, 0.01 µM or better.

Antibodies may also be produced by inducing in vivo production in the lymphocyte population or by screening recombinant immunoglobulin libraries or panels of highly specific binding reagents (Orlandi et al (1989) Proc Natl Acad Sci 86: 3833; and Winter and Milstein (1991) Nature 349: 293.

Antibody fragments which contain specific binding sites for the immunogens may also be generated. For example, such fragments include, but are not limited to, the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries may be constructed to allow rapid and easy identification of monoclonal Fab fragments with the desired specificity (Huse et al (1989) Science 256: 1275.

Administration of pharmaceutical compositions of the invention may be accomplished orally or parenterally. Methods of parenteral delivery include topical, intra-arterial (e.g. directly to the tumour), intramuscular, subcutaneous, intramedullary, intrathecal, intraventricular, intravenous, intraperitoneal, or intranasal administration. In addition to the active ingredients, these pharmaceutical compositions can contain suitable pharmaceutically acceptable carriers comprising excipients and other compounds that facilitate processing of the active compounds into preparations which can be used pharmaceutically. Further details on techniques for formulation and administration can be found in the latest edition of Remington's Pharmaceutical Sciences (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, etc, suitable for ingestion by the patient.

Pharmaceutical preparations for oral use can be obtained through combination of active compounds with solid excipient, optionally grinding a resulting mixture, and processing the mixture of granules, after adding suitable additional compounds, if desired, to obtain tablets or dragee cores. Suitable excipients are carbohydrate or protein fillers include, but are not limited to sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores can be provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterise the quantity of active compound (i.e. dosage).

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds can be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions can contain substances which increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes.

Optionally, the suspension can also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention can be manufactured in substantial accordance with standard manufacturing procedures known in the art (e.g. by means of conventional mixing, dissolving, granulating, dragee-making, levigating, emulsifying, encapsulating, entrapping or lyophilising processes).

The invention is further described below, for the purpose of illustration only, in the following examples:

EXAMPLE 1

Preparation of Tenascin-C, Fibronectin and Recombinant Fibronectin Proteins, and Syndecan Full length chicken tenascin-C TN260 was cloned by insertion of all known extra fibronectin type III repeats of tenascin-C into construct pCDNA/TN 190 (Fischer, D. et al (1995) J Biol Chem 270: 3378-3384) subcloned into the pCEP-Pu vector (Kohfeldt, E. et al (1997) FEBS Left 414: 557-561), transfected into human embryonic HEK-293 cells. Stable expressor cells were selected with puromycin. Recombinant tenascin-C was made by growing cells to ⅔ confluence in 10% FCS-containing medium. The medium was replaced by serum-free Dulbeccos's Modified Eagle Medium (DMEM) and conditioned medium was collected after 2 days. Conditioned medium was collected up to 6-times interrupted by 18 h of keeping cells in serum-containing medium between cycles. Recombinant tenascin-C was purified by immunoaffinity chromatography as described (Fischer, D et al (1995) J Biol Chem 270: 3378-3384). Conditioned medium was sequentially passed over columns of gelatin agarose, and Sepharose 4B (Pharmacia, Uppsala, Sweden) coupled with anti-tenascin-C (mAbM1) and (mAb60) (for antibodies see Fischer, D. et al (1997) Mol Biol Cell 8: 2055-2075). Bound tenascin-C washed with 0.05% Triton X-100, 1M NaCl, 0.01M Tris-HCl pH8.3, eluted with 50 mM diethylamine in PBS containing 0.01% Tween-20, and dialysed against 0.01% Tween-20 in PBS.

Fibronectin was prepared by gelatin agarose chromatography as described (Fischer, D. et al (1997) J Cell Sci 110: 1513-1522). Horse serum was passed over a gelatin agarose column, washed with 0.05% Triton X-100, 1M NaCl, 0.01M Tris-HCl pH8.3, eluted with 4M urea and dialysed against PBS. Recombinant fibronectin proteins were isolated on Ni-NTA resins according to the manufacturer's instructions (Quiagen).

The following recombinant proteins were obtained as indicated: FNIII13 (Bloom, L. et al (1999) Mol Biol Cell 10: 1521-1536), FNIII7-10 (Redick, S. D. et al (2000) J Cell Biol 149: 521-527), FNIII4-6 and FNIII12-15+CS and other fibronectin constructs (prepared according to the methods of Bloom, L. et al (1999), cDNAs for mouse syndecan-1 (Liu, W. et al (1988) J Biol Chem 273: 22825-22832), syndecan-2 (Klass, C. M. et al (2000) J Cell Sci 113: 493-506) and syndecan-4 (Oh, E. S. et al (1997) J Biol Chem 272: 11805-11811).

Fragments of FNIII13 having the amino acid sequence set forth in SEQ ID NO: 4 or the first ten amino acids thereof, were synthesized according to the common solid phase peptide synthesis method using t-Boc and Fmoc chemistry (see for example Chan, W. C. and White, P. D. (2000), Fmoc Solid Phase Peptide Synthesis: A Practical Approach, Oxford University Press, 368 pp., or Rovero, P. et. al. (1991) Int. J. Peptide Protein Res., 37, 140-4). The peptides were purified by HPLC (High pressure liquid chromatography) and verified using mass spectrometry.

EXAMPLE 2

Cell Lines, Cell Culture and Transfection

All cell lines were originally derived from ATCC if not mentioned otherwise; human KRIB osteosarcoma, MDA-MB435 breast carcinoma, T98G glioblastoma and Chinese hamster CHO-K1 and derivatives (Bauer, J. S et al (1992) J Cell Biol 116: 447-487 and Schreiner, C. L. et al (1989) J Cell Biol 109: 3157-3167). Cells were cultured in DMEM or αMEM with 10% FCS and antibiotics (0.36 mg/ml penicillin, 1 mg/ml streptomycin). Transfections were done with Fugene6 according to the manufacturer's protocol. For selection of stable syndecan-4 overexpressors T98G cells were grown with G418 and expression was analysed by immunofluorescence. Clonal lines were derived by limited dilution.

EXAMPLE 3

Adhesion Assay 60-well microtiter plates (Nunc) were coated with 10 μg/ml ECM molecules giving rise to 1 μg/cm$^2$ (fibronectin and tenascin-C) and 4 μg/cm$^2$ (FNIII13) for 1 h at 37° C. ECM proteins were coated separately, starting with fibronectin, followed by tenascin-C, FNIII13 and BSA. The non-coated plastic surface was blocked with 1% heat-inactivated BSA in PBS giving rise to 10 μg/cm$^2$ protein. Similarly, mixed substrata of collagen I and laminin 1, respectively with tenascin-C were prepared and tenascin-C was detected by ELISA.

Efficient fibronectin and tenascin-C coating was determined by ELISA with an anti-fibronectin and anti-tenascin-C antibody (Fischer, D. et al (1995) J Biol Chem 270: 3378-3384), respectively and by PAGE analysis of lysed surface-bound ECM material combined with Coomassie Brilliant Blue staining. Before plating, cells were serum starved for 18 h in DMEM containing 1×ITS (insulin, transferrin, selene) supplement, trypsinised, trypsin was blocked with 100 μg/ml soybean trypsin inhibitor in PBS and, cells were resuspended in serum-free medium and counted. 200-500 cells per well were plated for the indicated time points, fixed by addition of glutaraldehyde (2% final concentration) for 15 minutes and stained with 0.1% crystalviolet in 20% methanol for 30 minutes. Cells were observed under a Nikon microscope (Nikon diaphot) and pictures were taken with a Nikon camera.

EXAMPLE 4

DNA Replication and Proliferation Assay 96-well plates (Falcon) were coated as described above. Cells were serum starved overnight and trypsinised as described. $10^4$ cells were transferred onto the coated plates in the presence of the indicated mitogens. 14 h later cells were labelled with radioactive $^3$H-thymidine (0.5 μCi/well) for 4 h at 37° C., incorporated $^3$H-thymidine was precipitated with 10% TCA and determined with a Beckman scintillation counter after cell lysis in 0.3N NaOH, 2% SDS. For long-term cell proliferation assays $2\times10^3$ MDA-MB435 cells were plated into ECM-coated 96-well plates in the presence of 10 ng/ml insulin and incubated for the indicated time points in a humidified chamber at 37° C. in a $CO^2$-incubator. 50% fresh medium with growth factor was added every 24 h. At different time points cells were trypsinised and counted.

EXAMPLE 5

In Vitro Binding Assay (ELISA)

96-well ELISA plates were coated with the indicated ECM proteins for 1 h at 37° C., blocked with 1% milkpowder, 0.05% Tween-20 in PBS. ECM proteins were added at the indicated concentrations in blocking solution for 1 h, washed with blocking solution and anti-fibronectin or anti-tenascin-C antibodies were added. Bound proteins were detected by immune reaction with a peroxidase-coupled secondary antibody specifically recognising anti-fibronectin and anti-tenascin-C antibodies, respectively, followed by colour reaction with 21 mg/ml citric acid 1-hydrate, 34 mg/ml $Na_2HPO_4.2H_2O$, 0.4 mg/ml phenylenediamine, 1 µl $H_2O_2$ that was stopped with 4M sulphuric acid. The absorbance was read at 590 nm.

EXAMPLE 6

Immunofluorescence Microscopy $10^4$ cells were transferred onto 4-well Cellstar plastic plates (Greiner) that were coated with ECM proteins as described. Cells were fixed with 4% paraformaldehyde, 50 mM phosphate buffer, 5 mM EDTA in PBS for 15 minutes, blocked with 3% BSA, 0.5% Tween-20 in PBS and incubated with primary and secondary antibodies in blocking solution. Slides were embedded in 10.5% Mowiol containing 2.5% DABCO as antifade agent. Expression of syndecans was determined by immunofluorescence.

Cells were fixed in methanol and incubated with anti-syndecan-1, anti-syndecan-2 and anti-syndecan-4 antibodies at a dilution of 1:50 each, respectively. Cells were analysed by microscopy.

EXAMPLE 7

Tenascin-C Blocks Cell Attachment and Compromises Cell Spreading on Fibronectin Ten different tumour cell lines were plated on adhesive substrata such as fibronectin, collagen I and laminin 1, or on the large tumour-expressed form of tenascin-C (Borsi, L. et al (1992) Int J Cancer 52: 688-692) (see Table 1 below):

TABLE 1

| Cell Line | Time | TN | FN/TN | BSA |
|---|---|---|---|---|
| T98G | 1 h | 9.3 +/− 0.9 | 31.9 +/− 5.2 | 8.1 +/− 0.8 |
| MDA MB 435 | | 8.2 +/− 3.9 | 24.5 +/− 2.8 | 7.4 +/− 4.1 |
| T98G[a] | 20 h | 14.6 +/− 0.4 | 50.4 +/− 2.7 | 11.1 +/− 2.7 |
| MDA MB 435[b] | | 4.0 +/− 0.2 | 62.2 +/− 5.1 | 4.7 +/− 2.1 |
| CHO-K1[c] | | 4.7 +/− 0.2 | 37.9 +/− 2.1 | 7.4 +/− 1.4 |
| CHO-B2[c] | | 8.0 +/− 2.9 | 31.5 +/− 9.6 | 7.4 +/− 2.4 |
| CHO-B2α27[c] | | 4.3 +/− 0.7 | 45.1 +/− 3.7 | 8.1 +/− 2.1 |

Table 1 shows compromised cell adhesion by tenascin-C. The results of 1 h-attachment and 20 h-adhesion assays are summarized for the indicated tumour cell lines. Cells were plated in serum free medium or in medium supplemented with 40 ng/ml platelet-derived growth factor BB (PDGF-BB) (a), 100 ng/ml insulin (b) and ITS (c). The numbers of attached cells are described as % of cells attached on fibronectin.

Whereas most cells adhered to fibronectin, collagen I and laminin 1; less than 10% of cells attached on tenascin-C and remained rounded 1 h after plating showing that tenascin-C was not adhesive for all cell lines tested. Tenascin-C remained anti-adhesive for a long time, since all cells still failed to attach 20 h after plating in serum-free medium (see Table 1). Mitogen addition of PDGF-BB, insulin, endothelial growth factor (EGF), lysophosphatidic acid (LPA) and transforming growth factor-beta (TGFβ) did not reduce the anti-adhesiveness of tenascin-C (see Table 1).

In the tissue context cells are encountering tenascin-C in combination with other ECM molecules. An experiment was performed to establish whether tenascin-C would be anti-adhesive in a situation where cells were allowed to attach to an adhesive ECM such as fibronectin, laminin 1 or collagen I. Tenascin-C was found to compromise cell attachment when offered together with fibronectin both 1 h as well as 20 h after plating cells on a substratum containing equimolar amounts of tenascin-C and fibronectin (see Table 1). Even in a molar ratio of tenascin-C to fibronectin of 1:8 (that does not affect efficient coating of tenascin-C; see Example 9), tenascin-C blocked cell attachment on fibronectin as efficiently as in an equimolar ratio. In contrast to a mixed fibronectin/tenascin-C substratum, other substrata of collagen I and laminin 1 that contained equimolar amounts of tenascin-C were equally adhesive as without tenascin-C. Similar numbers of T98G cells and MRC-5 fibroblasts attached and spread on these mixed substrata as on the single ECM molecules. But on the mixed fibronectin/tenascin-C substratum only 45% of T98G cells were partially spread after 20 h. Tenascin-C blocks cell attachment and interferes with proper cell spreading on fibronectin, but not on collagen I nor laminin 1 in all cell lines tested. Tenascin-C enhances proliferation of a variety of tumour cell lines tested including glioblastoma and breast carcinoma cells. Thus in the tissue context tenascin-C appears to increase tumour mass by elevating the number of tumour cells. There was no evidence for an altered apoptosis rate but a higher proportion of cells on the fibronectin/tenascin-C mixture entered the DNA synthesis phase of the cell cycle than counterparts that were grown attached on fibronectin. Apparently, cells that were not yet determined to enter S-phase on fibronectin were triggered to start DNA synthesis upon tenascin-C compromised adhesion to fibronectin.

EXAMPLE 8

Increased Integrin Expression does not Overcome Compromised Cell Attachment by Tenascin-C The inventors tested whether expression of integrins capable of binding to fibronectin influences tenascin-C-induced compromised attachment on fibronectin. CHO-K1 cells (which express moderate levels of α5β1 (Bauer, J. S. et al (1992) J Cell Biol 116: 477-487)) were compared for levels of adhesion on fibronectin and other ECM substrates with that of cells that either express essentially no fibronectin binding integrins (CHO-B2), or overexpress α5β1 (CHO-B2α27) and αvβ1 (CHO-B2v7), respectively (Schreiner, C. et al (1991) Cancer Res 51: 1738-1740). Experiments showed that cell adhesion on the mixed substratum was blocked similarly in all cell lines irrespective of the nature of integrin expression (see Table 1); Also, overexpression of the α5β1 integrin in human HT29 colon carcinoma cells did not support cell attachment and spreading on the mixed fibronectin/tenascin-C substratum. β1 integrins are probably not the primary target of tenascin-C action.

EXAMPLE 9

Increased Tumour Cell Proliferation on a Mixed Fibronectin/Tenascin-C Substratum Cell proliferation and DNA synthesis of MDA-MB435 breast carcinoma, T98G glioblastoma, and Chinese hamster ovary carcinoma cells (CHO) grown on fibronectin, tenascin-C and on mixed fibronectin/tenascin-C substrata was determined. MDA-MB435 breast carcinoma cells were grown on fibronectin or on an equimolar mixture of fibronectin and tenascin-C in the presence of 100 ng/ml insulin. After 27 h, 51 h, and 75 h cells were counted. 24% and 33% more cells were counted on fibronectin/tenascin-C than on fibronectin after 51 h and 75 h of culturing, respectively. T98G glioblastoma cells were cultured on fibronectin, collagen I, laminin 1 and on mixtures of these ECM molecules with tenascin-C in the presence of 40 ng/ml PDGF-BB. $^3$H-thymidine incorporation per attached cell was measured as fold over cpm on fibronectin. The DNA replication indices (cpm/cell) of MDA-MB435 and T98G cells were about 2- and 3-fold increased on the mixed fibronectin/tenascin-C substratum in comparison to fibronectin alone (see Table 2 below).

TABLE 2

| Cell Line | TN | FN/TN |
| --- | --- | --- |
| T98G$^a$ | 3.0 +/− 0.9 | 3.0 +/− 0.2 |
| MDA MB 435$^b$ | 2.7 +/− 0.6 | 1.8 +/− 0.6 |
| CHO-K1$^c$ | 5.9 +/− 1.7 | 2.3 +/− 0.2 |
| CHO-B2$^c$ | 7.1 +/− 0.2 | 2.6 +/− 0.3 |
| CHO-B2α27$^c$ | 11 +/− 3.9 | 2.5 +/− 0.6 |

Table 2 shows enhanced DNA synthesis by tenascin-C. DNA replication was determined by $^3$H-thymidine incorporation and is described as relative increase in cpm over cells plated on fibronectin. Serum starved cells were triggered to enter S-phase by 40 ng/ml PDGF-BB (a), 100 ng/ml insulin (b) and ITS (c).

The possibility that rounded cells might have taken up more $^3$H-thymidine than attached cells could be ruled out as similar total cellular cpm were counted from cells plated on the different substrata after 4 h when T98G cells would not have entered S-phase. Increased DNA synthesis levels were also observed for the other tumour cell lines tested (see Table 2). This demonstrated that a mixed fibronectin/tenascin-C substratum triggered more cells to enter S-phase of the cell cycle than fibronectin alone. Since all tumour cell lines tested were equally compromised in cell adhesion on a mixed fibronectin/tenascin-C substratum two representative cell lines, human MDA-MB435 breast carcinoma and T98G glioblastoma cells were chosen for further study.

In order to address whether tenascin-C alone and in ECM contexts other than fibronectin might also enhance proliferation, an investigation was carried out into DNA synthesis on a pure tenascin-C substratum where cells remained rounded and, on mixed substrata of collagen I and laminin 1 that contained tenascin-C where cells spread normally. These experiments revealed that the DNA replication indices of all cell lines tested were increased with levels as high as 11-fold on pure tenascin-C (see Table 2). However, on adhesive substrata containing tenascin-C (mixtures with collagen I and laminin 1, respectively), DNA synthesis rates were identical to those on the single ECM molecules. To rule out that tenascin-C may shorten S-phase of the cell cycle in tumour cells, DNA synthesis of T98G cells was determined by assay every two hours starting 11 h after plating. Therefore, T98G glioblastoma cells were grown on fibronectin or on a mixture of fibronectin and tenascin-C in the presence of 40 ng/ml PDGF-BB, labelled with $^3$H-thymidine for 1 h and harvested and counted every two hours starting 11 h after plating. This experiment revealed that on the mixed substratum DNA replication followed similar kinetics as on fibronectin. These observations show that tenascin-C stimulates a subset of cells to enter S-phase of the cell cycle by interfering with fibronectin-specific cell adhesion signalling.

EXAMPLE 10

Tenascin-C Binds to the 13$^{th}$ Fibronectin Type III Repeat of the HepII Site in Fibronectin The anti-adhesive and proliferation-stimulatory effect of tenascin-C was found to be specific for cells on a mixed fibronectin/tenascin-C substratum. An ELISA assay was performed (see Example 5), and it was shown that fibronectin binds to substratum-immobilised tenascin-C in a dose-dependent manner. Further ELISA assays showed that recombinant fragments FNIII 4-6, FN12-15+CS and FNIII13 that are part of the heparin and cell binding sites HepIII and HepII in fibronectin respectively bound to tenascin-C in a dose-dependent manner reaching saturation (e.g. FNIII13). Bound fragments were detected with a polyclonal anti-fibronectin antibody, bound tenascin-C was detected with a monoclonal anti-tenascin-C antibody.

Tenascin-C and FNIII13 were also found to form complexes in co-immunoprecipitation experiments. Moreover, binding of tenascin-C to surface-immobilised intact fibronectin could be competed for by FNIII13 in a concentration-dependent fashion. No binding of the recombinant fragment FNIII7-10, including the RGD and synergy sites, to tenascin-C was detected in an ELISA assay. This shows that binding of tenascin-C to FNIII13 in the HepII site of fibronectin was specific.

EXAMPLE 11

The 13$^{th}$ Fibronectin Type III Repeat Restores the Tenascin-C-Induced Cell Spreading Defect on Fibronectin Attachment assays showed that the majority of T98G cells, MDA-MB435 cells and rat embryo fibroblasts REF52 spread on a triple matrix of fibronectin/tenascin-C/FNIII13. Cells were plated on substrata (FN, FN/TN, FN/TN/III13, FN/TN+III13, III13, or BSA) for 1 h and 2 h, fixed and stained with crystal violet or vinculin and TRITC—labelled phalloidin. Adherent cells were photographed and spread cells were counted. Six-fold molar excess of FNIII13 (4 μg/cm$^2$) was either bound to a mixed fibronectin/tenascin-C substratum prior to addition of the cells (FN/TN/III13) or, was added in solution together with the cells (FN/TN+FNIII13). Proliferation of MDA-MB435 cells and DNA replication of T98G glioblastoma cells were determined as described in Examples 4 and 5. This revealed that FNIII13 could restore the cell spreading defect caused by tenascin-C in all cell lines tested. The FNIII13 fragment did not provide any spreading signal by itself because cells poorly attached and remained rounded on a FNIII13 substratum. Cell spreading was also restored when cells were added to a fibronectin/tenascin-C substratum together with soluble FNIII13. In contrast to FNIII13, FNIII4-6 did not restore cell spreading on fibronectin/tenascin-C, even when offered immobilised or in solution. These results were confirmed by analysing the cytoskeleton and adhesion structures of cells plated on the different substrata. T98G cells plated for 2 h on fibronectin or on the mixed substratum were stained for vinculin. Focal contacts were found to have formed on fibronectin but not on fibronectin/tenascin-C. In addition, polymerisation of actin into stress fibres was blocked by tenascin-C. No polymerised actin was found.

Since the FNIII13 fragment restored cell spreading on fibronectin/tenascin-C an experiment was performed to see whether actin stress fibres and focal contacts were restored by FNIII13. Immunofluorescence experiments revealed that FNIII13 largely restored actin stress fibres and focal contacts in T98G and REF52 cells upon addition of the FNIII13 fragment to a fibronectin/tenascin-C substratum.

Tenascin-C specifically interferes with cell attachment and spreading on fibronectin. Tenascin-C compromised focal contact and actin stress fibre formation, both of which are hallmarks of integrin mediated cell adhesion. In addition, β1 integrins did not localize to focal contacts and, neither integrin activation by $MnCl_2$ nor overexpression of the α5β1 integrin caused reversion of the tenascin-C phenotype. Tenascin-C affects integrin function by an indirect mechanism.

Tenascin-C binds to fibronectin specifically to the HepII and HepIII cell binding sites in fibronectin. Recombinant fragments including the HepIII (FNIII4-6) and HepII (FNIII12-15+CS, FNIII13) sites of fibronectin bind tenascin-C in a dose-dependent and competable (FNIII13) manner. In contrast, a fragment encompassing the RGD and synergy cell binding site (FNIII7-10) does not bind tenascin-C. Whereas FNIII4-6 does not affect cell spreading of T98G cells, FNIII13 neutralizes the spreading defect and restores focal contacts and actin stress fibre formation on the mixed substratum of fibronectin and tenascin-C. Tenascin-C efficiently blocks cell access to fibronectin by directly binding to the cell binding site located in FNIII13, thereby inhibiting full cell spreading.

In summary, tenascin-C interferes with cell spreading, focal contact and actin stress fibre formation on fibronectin and this effect can be neutralised by the addition of FNIII13.

EXAMPLE 12

Fragments of the 13$^{th}$ Fibronectin Type III Repeat Restore the Tenascin-C-Induced Cell Spreading Defect on Fibronectin As described in Example 11, it could also be shown that the recombinant fragment of FNIII13 having the amino acid sequence set forth in SEQ ID NO:4 restored cell spreading on fibronectin/tenascin-C. Immunofluorescence experiments revealed that the recombinant fragment of FNIII13 having the amino acid sequence set forth in SEQ ID NO:4 also largely restored actin stress fibres and focal contacts in T98G and REF52 cells upon addition of the recombinant fragment to a fibronectin/tenascin-C substratum.

Therefore, tenascin-C efficiently blocks cell access to fibronectin by directly binding to the binding site located in the recombinant fragment of FNIII13 having the amino acid sequence set forth in SEQ ID NO:4, thereby inhibiting full cell spreading. Tenascin-C interferes with cell spreading, focal contact and actin stress fibre formation on fibronectin and this effect can be neutralised by the addition of the recombinant fragment of FNIII13 having the amino acid sequence set forth in SEQ ID NO:4.

The same experiments were performed using the recombinant fragment of FNIII13 having the first ten amino acids of the amino acid sequence set forth in SEQ ID NO:4 and similar results were obtained but to a lesser effect.

EXAMPLE 13

The 13$^{th}$ Fibronectin Type III Repeat Neutralises the Cell Proliferation Stimulatory Effect of Tenascin-C Since detachment by tenascin-C correlated with enhanced tumour cell proliferation, and FNIII13 restored cell spreading, an experiment was performed to see whether FNIII13 also reduced proliferation of cells on the mixed substratum to levels as on fibronectin. This was confirmed. Similar numbers of MDA-MB435 breast carcinoma cells were counted on the triple matrix containing FNIII13 as on fibronectin alone 75 h after plating and for T98G cells similar DNA synthesis levels were determined on fibronectin/tenascin-C/FNIII13 as on fibronectin.

The same experiment was performed to see whether the peptide of the sequence set forth in SEQ ID NO:4 also reduced proliferation of cells on the mixed substratum to levels as on fibronectin which was confirmed. Similar numbers of MDA-MB435 breast carcinoma cells were counted on the triple matrix containing the recombinant fragment of FNIII13 having the amino acid sequence set forth in SEQ ID NO:4 as on fibronectin alone 75 h after plating and for T98G cells similar DNA synthesis levels were determined on fibronectin/tenascin-C/fragment of FNIII13 as on fibronectin.

The same experiment was performed with the recombinant fragment of FNIII13 having the first ten amino acids of the amino acid sequence set forth in SEQ ID NO:4.

EXAMPLE 14

Overexpression of Syndecan-4 Restores Cell Spreading on a Mixed Fibronectin/Tenascin-C Substrate An experiment was performed to check for the possibility that tenascin-C might compete with syndecan-4 for binding to the HepII site in fibronectin. The experiment tested whether activation of syndecan-4 through overexpression could rescue the tenascin-C-induced spreading defect on fibronectin. Parent T98G cells, pools (T98G:S4) or a selected clone (T98G:S4*) of glioblastoma cells stably overexpressing syndecan-4 (T98G:S4) were plated on the indicated substrata for 30 minutes, 2 h, 18 h or fixed, stained with crystal violet, photographed, and counted or stained with TRITC-labelled phalloidin and vinculin. Syndecan-4 was detected by immunofluorescence with an anti-syndecan-4 antibody. There was no staining with an unspecific anti-His monoclonal antibody (control), nor with the secondary antibody alone. FAK (focal adhesion kinase) autophosphorylation at Y397 and total FAK expression levels were assessed by immunoblotting with specific antibodies. DNA replication was determined as described in Example 4 and 5. As a result, pools of T98G cells (T98G:S4) that overexpressed syndecan-4 thereby activating syndecan-4 attached and spread on the mixed fibronectin/tenascin-C substratum. The majority of the 64.7% of T98G:S4 cells that attached also spread on the fibronectin/tenascin-C substratum. This was in contrast to T98G cells with low endogenous syndecan-4 expression levels, that only spread to a minimal extent (3.5%) on a mixed substratum. Spreading of the syndecan-4-overexpressing clone T98G:S4* was completely restored on the mixed fibronectin/tenascin-C substratum 2 h after plating.

In addition to stimulating cell attachment and spreading on the mixed fibronectin/tenascin-C substratum, overexpression of syndecan-4 in clonal T98G:S4* also completely restored focal contact formation and actin polymerisation into stress fibres. This observation supports a function of syndecan-4 in cell spreading linked to Rho-mediated actin stress fibre formation as recently has been shown by Saoncella, S. et al (1999) P.N.A.S. 96: 2805-2810. Activation of focal adhesion kinase (FAK) by autophosphorylation at Y397 is an early step in cell adhesion signalling. This is compromised in T98G parental cells and in T98G:S4* cells on a fibronectin/tenascin-C substratum. In contrast, plating on a substratum of fibronectin/tenascin-C that contains FNIII13 largely restored FAK autophosphorylation indicating that activation of syndecan-4 by FNIII13 is linked to restoration of cell adhesion signalling by FNIII13. In addition to rescuing cell spreading on a mixed fibronectin/tenascin-C substratum overexpression of syndecan-4 also reduced DNA replication levels to that on fibronectin.

Overexpression of syndecan-4 in T98G cells rescued the spreading defect and the lack of actin stress fibre formation on the mixture of fibronectin and tenascin-C. This was specific for syndecan-4 since overexpression of syndecans-1 and -2 did not neutralize the tenascin-C-induced phenotype. We showed that both the addition of FNIII13 and the overexpression of syndecan-4 restored tenascin-C-compromised cell spreading on fibronectin. Therefore, FNIII13 neutralization of the tenascin-C effect is mediated through syndecan-4 and that within the characterized syndecan-4 recognition sequence in fibronectin (FNIII12-15) (Woods, A. et al (2000) Arch Biochem Biophys 374: 66-72) binding of syndecan-4 occurs through FNIII13. Also, FNIII13 binds to syndecan-4 overexpressing T98G cells in a dose-dependent and heparin-competable manner. Syndecan-4 binds to the same site in fibronectin as tenascin-C (FNIII13) and the interaction of tenascin-C with FNIII13 competes with syndecan-4 binding. FNIII14 is not relevant for the tenascin-C induced cell spreading defect since addition of FNIII13 alone was sufficient to restore cell spreading.

The blocking of syndecan-4 function by tenascin-C enhances tumour cell proliferation. The inventors conclude that higher levels of syndecan-4 in glioblastoma and breast cancer cells can attenuate tumour cell proliferation in the context of fibronectin and tenascin-C.

EXAMPLE 15

The 13$^{th}$ Fibronectin Type III Repeat (FNIII13) of Fibronectin Binds to Syndecan-4

To investigate FNIII13 as a potential ligand of syndecan-4, the interaction of syndecan-4 with FNIII13 was tested. Upon addition of FNIII13 to T98G:S4* cells, FNIII13 was detected in a syndecan-4 immunoprecipitation followed by western blotting with a GST specific antibody. This interaction was blocked upon addition of heparin. Parental and syndecan-4 overexpressing T98G:S4* cells were incubated with (100 µg/ml) FNIII13 for 1 h in the presence or absence of 0.5 mg/ml heparin. Syndecan-4-bound FNIII13 was detected by immunoprecipitation of syndecan-4 and immunoblotting for FNIII13. Recombinant FNIII13 was added to the cells in the absence or presence of (0.5 mg/ml) heparin. This shows that FNIII13 is a ligand for syndecan-4. To further test whether FNIII13 binds to syndecan-4, FNIII13 was added to T98G cells and cell surface-bound FNIII13 was detected by pull down of the GST-tagged FNIII13 with glutathione Sepharose followed by western blotting with an anti-His antibody or by immunofluorescence with an anti-GST antibody. FNIII13 bound to the cell surface of T98G:S4* with several fold increased levels compared to parental T98G, but not to T98G:S1 and T98G:S2 cells (which overexpress syndecan-1 and syndecan-2 respectively, see below). This interaction could be blocked by heparin showing that syndecan-4 bound FNIII13 in a glycosaminoglycan-dependent manner. In addition, cell surface-bound FNIII13 was detected by immunofluorescence with an anti-His and anti-GST antibody. To test whether overexpression of syndecans-1 and -2 could also rescue the tenascin-C-specific cell spreading defect. T98G cells that stably overexpress syndecan-1 (T98G:S1) and -2 (T98G:S2) were generated and were plated for 2 h on fibronectin/tenascin-C. In contrast to syndecan-4, neither syndecan-1 nor syndecan-2 overexpression allowed cells to spread on the mixed substratum. Like T98G:S4*, syndecan-1 and -2 overexpressors did not bind to FNIII13, nor to tenascin-C. Syndecan overexpression in T98G:S1 and T98G:S2 was demonstrated by immunofluorescence with syndecan-1 and -2 specific antibodies. Syndecan-2 expression was determined by incubation with chicken anti-syndecan-2, followed by rabbit anti-chicken and FITC coupled goat anti-rabbit immunostaining.

Rescue of cell spreading was only accomplished by activation of syndecan-4 and not by syndecans-1 or -2. FNIII13 is therefore a ligand for syndecan-4 and tenascin-C specifically competes with binding of syndecan-4 to FNIII13 and thereby prevents cell spreading on fibronectin.

EXAMPLE 16

Fragments of the 13$^{th}$ Fibronectin Type III Repeat (FNIII13) of Fibronectin Bind to Syndecan-4

The same experiment as described in Example 15 is performed to investigate the recombinant fragment of FNIII13 having the amino acid sequence set forth in SEQ ID NO:4, and the fragment having the first ten amino acids of the sequence set forth in SEQ ID NO:4, as a potential ligand of syndecan-4.

The invention claimed is:

1. A pharmaceutical composition comprising a pharmaceutically acceptable excipient, diluent or carrier and a portion of a polypeptide, wherein said portion is the amino acid sequence set forth in SEQ ID NO: 4 which interferes with tenascin binding to fibronectin.

2. The pharmaceutical composition as claimed in claim 1, wherein said portion is capable of restoring syndecan signalling.

3. The pharmaceutical composition as claimed in claim 2, wherein the syndecan signalling is mediated by syndecan-4.

4. The pharmaceutical composition as claimed in claim 1, wherein said portion binds to tenascin.

5. The pharmaceutical composition as claimed in claim 1, wherein said portion binds to tenascin C.

6. The pharmaceutical composition as claimed in claim 1 wherein said portion further binds to syndecan.

7. The pharmaceutical composition as claimed in claim 1, wherein said portion competes with the 13th fibronectin type III repeat of the native fibronectin protein for tenascin binding.

8. The pharmaceutical composition as claimed in claim 1, wherein said portion is recombinant.

9. The pharmaceutical composition as claimed in claim 1 wherein said portion further binds to syndecan-4.

* * * * *

SEQUENCE LISTING

<160> NUMBER OF SEQ ID NOS: 4

<210> SEQ ID NO 1
<211> LENGTH: 89
<212> TYPE: PRT
<213> ORGANISM: Homo sapiens

<400> SEQUENCE: 1

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
            35                  40                  45

Ile Lys Pro Asp Val Arg Ser Tyr Thr Ile Thr Gly Leu Gln Pro Gly
        50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 2
<211> LENGTH: 49
<212> TYPE: PRT
<213> ORGANISM: Homo sapiens

<400> SEQUENCE: 2

Arg Arg Ala Arg Val Thr Asp Ala Thr Glu Thr Ile Thr Ile Ser
1               5                   10                  15

Trp Arg Thr Lys Thr Glu Thr Ile Thr Gly Phe Gln Val Asp Ala Val
                20                  25                  30

Pro Ala Asn Gly Gln Thr Pro Ile Gln Arg Thr Ile Lys Pro Asp Val
            35                  40                  45

Arg

<210> SEQ ID NO 3
<211> LENGTH: 20
<212> TYPE: PRT
<213> ORGANISM: Homo sapiens
<220> FEATURE:
<223> OTHER INFORMATION: Sequence at position 3 can be any amino acid
      residue.
<223> OTHER INFORMATION: Sequence at positions 5-17 can be any amino
      acid residue.
<223> OTHER INFORMATION: Sequence at position 19 can be any amino acid
      residue.

<400> SEQUENCE: 3

Arg Arg Xaa Arg Xaa Xaa Xaa Xaa Xaa Xaa Xaa Xaa Xaa Xaa Xaa Xaa
1               5                   10                  15

Xaa Arg Xaa Lys
            20

<210> SEQ ID NO 4
<211> LENGTH: 20
<212> TYPE: PRT
<213> ORGANISM: Homo sapiens

<400> SEQUENCE: 4

Arg Arg Ala Arg Val Thr Asp Ala Thr Glu Thr Ile Thr Ile Ser
1               5                   10                  15

Trp Arg Thr Lys
            20